US006048529A

United States Patent [19]

Atassi et al.

[11] Patent Number: 6,048,529

[45] **Date of Patent: *Apr. 11, 2000**

[54] PVA OR PEG CONJUGATES OF PEPTIDES FOR EPITOPE-SPECIFIC IMMUNOSUPPRESSION

[76] Inventors: M. Zouhair Atassi, 11743 Cawdor Way, Houston, Tex. 77024; Tetsuo Ashizawa, 3435 Westheimer Rd., #301, Houston, Tex. 77027

[ * ] Notice: This patent issued on a continued prosecution application filed under 37 CFR 1.53(d), and is subject to the twenty year patent term provisions of 35 U.S.C. 154(a)(2).

[21] Appl. No.: 08/414,174

[22] Filed: Mar. 29, 1995

Related U.S. Application Data

[63] Continuation of application No. 07/811,050, Dec. 19, 1991, abandoned.

[51] Int. Cl.[7] ........................ A61K 39/385; A61K 38/00; C07K 5/00; C07K 16/00

[52] U.S. Cl. .................................... 424/193.1; 424/193.1; 424/194.1; 424/278.1; 530/300; 530/326; 530/327; 530/333; 530/334; 530/335; 530/344

[58] Field of Search ............................. 424/193.1, 194.1, 424/278.1; 530/300, 326, 327, 335, 344, 334, 333

[56] References Cited

U.S. PATENT DOCUMENTS

| | | |
|---|---|---|
| 4,261,973 | 4/1981 | Lee et al. . |
| 5,068,177 | 11/1991 | Carson et al. . |
| 5,130,297 | 7/1992 | Sharma et al. . |
| 5,194,425 | 3/1993 | Sharma et al. . |
| 5,256,641 | 10/1993 | Yatvin et al. . |
| 5,260,422 | 11/1993 | Clark et al. . |
| 5,268,454 | 12/1993 | Barstad et al. . |
| 5,284,935 | 2/1994 | Clark et al. . |
| 5,370,871 | 12/1994 | Dintzis et al. . |
| 5,468,481 | 11/1995 | Sharma et al. . |
| 5,468,730 | 11/1995 | Hahn . |
| 5,552,529 | 9/1996 | Rearden . |
| 5,578,496 | 11/1996 | Atassi et al. . |
| 5,614,192 | 3/1997 | Vandenbark . |
| 5,759,834 | 6/1998 | Atassi . |
| 5,800,815 | 9/1998 | Chestnut et al. . |

FOREIGN PATENT DOCUMENTS

| | | |
|---|---|---|
| 85306855 | 9/1985 | European Pat. Off. . |
| 0 247 860 A2 | 12/1987 | European Pat. Off. ........ A61K 37/02 |
| 89105728 | 3/1989 | European Pat. Off. . |
| 89107960 | 3/1989 | European Pat. Off. . |
| 0365087 | 10/1989 | European Pat. Off. . |
| 90109907 | 5/1990 | European Pat. Off. . |
| 0432691 | 12/1990 | European Pat. Off. . |
| 0 473 084 A2 | 8/1991 | European Pat. Off. ........ C08G 65/32 |
| 2 566 780 | 1/1986 | France . |
| 24 55 623 | 11/1974 | Germany . |
| 1469472 | 7/1973 | WIPO . |
| PCTUS9002144 | 4/1990 | WIPO . |
| 9218150 | 10/1992 | WIPO . |
| 9309810 | 5/1993 | WIPO . |

OTHER PUBLICATIONS

Suppression of Reaginic Antibodies with Modified Allergens, "III. Preparation of Tolerogenic Conjugates of common Allergens with Monomethoxypolyethylene Glycols of Different Molecular Weights by the Mixed Anhydride Method," by S.I. Wie, C.W. Wie, W.Y. Lee, L.G. Filion, A.H. Sehon and E. Akerblom, International Archives of Allergy and Applied Immunology, vol. 64 (1981).

Suppression of Reaginic Antibodies with Modified Allergens, III. Down–regulation of secondary in vitro antibody responses by suppressor T cells of mice treated with a tolerogenic conjugate of ovalbumin and monomethoxypolyethylene glycol, OVA (mPEG)$_{13}$, by S. suppressor T cells of mice treated with a tolerogenic conjugate of ovalbumin and monomethoxypolyethylene glycol, OVA(mPEG)$_{13}$, by S. Mokashi, V. Holford–Strevens, G. Sterrantino, C.J.C. Jackson and A.H. Sehon, Immunology Letters, 23 (1989/1990) 95–102.

Preparation and Immunochemical Properties of Methoxypolyethylene Glycol–Coupled and N–Carboxymethylted Derivatives of Ragweed Pollen Allergen, Antigen E[1], by TePiao King, Loucia Kochoumian, and Lawrence M. Lichtenstein, Archives of Biochemistry and Biophysics, Lawrence M. vol. 178, pp. 442–450 (1977).

Abrogation of reaginic antibodies with modified allergens, by Weng Y. Lee and Alec H. Sehon, Nature, vol. 267, pp. 618–619, Jun. 16, 1977.

Suppression of Reaginic Antibodies with Modified Allergens, "IV. Induction of Suppressor T Cells by Conjugates of Polyethylene Glycol (PEG) and Monomethoxy PEG with Ovalbumin," by W.Y. Lee, A.H. Sehon and E. Akerblom, International Archives of Allergy and Applied Immunology, vol. 64, pp. 100–114 (1981).

Suppression of Reaginic Antibodies with Modified Allergens, "I. Reduction in Allergenicity of Protein Allergens by Conjugation to Polyethylene Glycol," by Weng Y. Lee and Alec H. Sehon, International Archives of Allergy and Applied Immunology, vol. 56, pp. 193–206 (1978).

(List continued on next page.)

*Primary Examiner*—Nita Minnifield
*Attorney, Agent, or Firm*—C. Steven McDaniel; Conley, Rose & Tayon, P.C.

[57] ABSTRACT

The invention relates to a procedure for synthesis of well-defined conjugates of peptides to the tolerogenic polymer monomethoxypolyethylene glycol (mPEG) or polyvinyl alcohol (PVA). This method results in the preparation of conjugates in which one molecule of tolerogenic polymer is specifically coupled to one or the other or both of the termini of an otherwise unaltered peptide molecule. A synthetic peptide synthesized using this method and corresponding to a myasthenogenic region of an acetylcholine receptor was conjugated to monomethoxypolyethylene glycol. Injection of animals with the mPEG-conjugate and subsequent immunization with whole receptor suppressed the development of experimental autoimmune myasthenia gravis (EAMG) by electrophysiological criteria. Specifically-conjugated, tolerogenic peptides are also disclosed for diseases as diverse as ragweed pollen allergy and Grave's disease.

21 Claims, 11 Drawing Sheets

OTHER PUBLICATIONS

Suppression of Reaginic Antibodies with Modified Allergens, "II. Abrogation of Reaginic Antibodies with Allergens Conjugated to Polyethylene Glycol," by Weng Y. Lee and Alec H. Sehon, International Archives of Allergy and Applied Immunology, vol. 56, pp. 193–206 (1978).

Hyposensitization in asthmatics with mPEG–modified and unmodified house dust mite extract, "IV. Occurrence and prediction of side effects," by H. Mosbech, A. Dirksen, S. Dreborg, L. Frolund, J.H. Heinig, U.G. Svendsen, M. Soborg, E. Taudorf & B. Weeke, Allergy, No. 45, pp. 142–150 (1990).

Modulation of Antibody Responses by Conjugates of Antigens With Monomethoxypolyethylene Glycol, by Alec. H. Sehon, Immunobiology of Proteins and Peptides V Vaccines, pp. 341–351.

New Model Visual Pigments, Spectroscopy of Poly(ethylene glycol) Peptide Schiff bases of Retinal, by P.K. Das, Ralph S. Becker, Dieter Hannak, and Ernst Baver, Journal of the American Chemical Society, vol. 101, No. 1, Jan. 3, 1979.

Soluble Polymers in Organic Syntheses: II. Use of Polyethylene Glycol–Bound Reagents for Peptide Syntheses, by Manfred Mutter, Tetrahedron Letters, No. 31, Jul. 1978.

Syntheses of Poly(ethylene Glycol)–Bound NADP by Selective Modification at the 6–amino group of NADP, by Keiko Okuda, Itaru Urabe, and Hirosuke Okada, European Journal of Biochemistry, vol., 151, No. 1, Aug. 11, 1985.

A Poly(oxyethylene)–Supported Cys–Pro–Leu–Cys/Fe(II) Complex as a Rubredoxin Model: Protection of the Fe–Cys Coordination from Hydrolysis in Aqueous Solution, by Norikazu Ueyama, Michio Kanata, and Akira Nakamura, Polymer Journal, vol. 17, No. 5, pp. 721–727 (1985).

Development of new Functionalized Polymers and Their Utilization in Peptide Chemistry, by Shmuel Zalipsky, Ph.D., University of Minnesota (1987), Dissertation Abstracts International (The Sciences and Engineering), vol. 48, No. 8 (Feb. 1988).

Engineering Proteins to Enhance Their Partition Coefficients in Aqueous Two–Phase Systems, by Kristina Kohler, Charlotta Ljungquist Akihiko Kondo, Andres Veide, and Bjorn Nilsson, Biotechnology, vol. 9, No. 7, Jul. 1991.

Preparation of Polyethylene Glycol Derivatives with two Different Functional groups at the Termini, by Shmuel Zalipsky and George Barany, Polymer Preprints, vol. 27, No. 1, Apr. 1986.

Investigation into the Spectroscopy and Photoisomerization of a Series of Ploy(Ethylene Glycol) peptide Schiff Bases of 11–cis Retinal, by Kenn Freedman, Ralph S. Becker, Dieter Hannak, and Ernst Bayer, Photochemistry and Photobiology, vol. 43, No. 3, Mar. 1986.

Modification of Batroxobin with Activated Polyethylene Glycol: Reduction of Binding Ability Towards Anti–Batroxobin Antibody and Retention of Defibrinogenation Activity in Circulation of Preimmun–Dogs, by Hiroyuki Nushimura, Katsunobu Takahashi, Katsukiyo Sakurai Kazunobu Fujinuma, Yasushi Imamura, Mitsuoki Ooba, and Yuji Inada, Life Sciences, vol. 33, No. 15, Oct. 10, 1983.

A Double–Blind Study Comparing Monomethoxy Polyethylene Glycol–Modified Honeybee Venom and Unmodified Honeybee Venom for Immunotherapy, by Ulrich Muller, M.D., Arthur R. Rabson, M.R.C.Path., Marium Bischof, M.D., Ruth Lomnitzer, Ph.D., Sten Dreborg, M.D., and Ake Lanner, M.Sc., The Journal of Allergy and Clinical Immunoology, vol. 80, No. 1 (1987).

Synthesis, Isolation, and Characterization of Conjugates of Ovalbumin with Monomethoxypolyethylene Glycol Using Cyanuric Chloride as the Coupling Agent, by Chung–Ja C. Jackson, James L. Charlton, Kimberly Kuzminski, Glen M. Lang, and Alex H. Sehon, Analytical Biochemistry, vol. 165, pp. 114–127 (1987).

A convenient general Method for synthesis of $N_x$ or $N^w$ Dithiasuccinoyl (Dts) Amino Acids and Dipeptides: Application of Polyethylene Glycol as a Carrier for Functional Purification, by Shmuel Zalipsky, Fernando Albericio, Utszula Slomczynska, and George Barany.

Characterization of a Polyethylene Glycol Conjugate of Recombinant Human Interferon, by Kita Yoshiko, Michael F. Rohde, Rsutomu Arakawa, Katerina D. Fagin, Eleanor N. Fish, and Kris Banerjee, Drug Design and Delivery, vol. 6, pp. 157–167 (1990).

Soluble Polymers in Organic Syntheses 3. Polyethylene Glycol as Acid Labile Solubilizing Protecting Group, by h. Anzinger and M. Mutter, Polymer Bulletin, No. 66, Nov. 22, 1982.

Enzyme Modification by MPEG with an Amino Acid or Peptide as Spacer Arms, by Luciana Sartore, Paolo Caliceti, Oddone Schiavon, and Francesco M. Veronese, Applied Biochemistry and Biotechnology, vol. 27, No. 1, Jan. 1991.

Tsuji, Hisashi et al., "Modified Interleukin–2", English language Abstract of Japanese Patent No. 63,258,896 in *Chemical Abstracts*, vol. 111, Oct. 9, 1989, No. 15 p. 610.

Sehon. Prog. Allergy 32:161–202, 1982.

Atassi etal Eur. J. Immunol. 16:229–235, 1986.

Engel. 1984. Ann. Neurol. 16:519–534.

Lindstrom et al. 1988 Adv. in Immunol. 42:233–84.

Hohfield et al. 1987. PNAS (USA) 84:5379–83.

Tzartos et al. 1980. PNAS (USA) 77(2):755–59.

Hohfeld et al. 1988. J. Clin. Invest. 81:657–660.

Killen et al. 1984. J. Immunol. 133(5):2549–53.

Devillers–Thiery et al. 1983. PNAS (USA) 80:2067–71.

Noda et al. 1982. Nature. 299:793–97.

Sumikawa et al. 1982. Nuc. Acid. Res. 10(19):5809–22.

Hohfeld et al. 1986. Neurology. 36:618–21.

Wunoch et al. 1991. Int. J. Peptide Prot. Res. 37:90–102.

Atassi et al. 1991. PNAS(USA) 88:3613–17.

Mulac–Jericevic et al. 1987. PNAS(USA) 84:3633–36.

Kao et al. 1986. JBC. 261(18):8085–88.

Oshima et al. 1990. Eur. J. Immunol. 20:2563–69.

King et al. J. Exp. Med. 149:424–35. 1979.

Sehon et al. 1988. Adv. Exp. Med. Biol. 251:341–351.

Atassi, M.Z. et al (91a) J. Protein Chem. 10:623–627.

Atassi, M.Z. et al (92) Proc. Natl. Acad. Sci USA 89:5852–5856.

Schwarz, R.S. et al (89) in *Fundamental Immunology*, W.E. Paul, ed. (New York, NY) pp. 851–852.

1. Gly.Lys.Val.Tyr.Leu.Val.Gly.Gly.Pro.Glu.Leu.Gly.Gly.Trp.Lys

2. Glu.Val.Trp.Arg.Glu.Glu.Ala.Tyr.His.Ala.Cys.Asp.Ile.Lys.Asp

3. Pro.Gly.Gly.Pro.Asp.Arg.Phe.Thr.Leu.Leu.Thr.Pro.Gly.Ser.His

4. Thr.Pro.Gly.Ser.His.Phe.Ile.Cys.Thr.Lys.Asp.Gln Lys.Phe.Val

5. $H_2N$-Lys.Ser.Tyr.Cys.Glu.Ile.Ile.Val.Thr.His.
Phe
.
HO-Ile.Gly.Leu.Lys.Met.Thr.Cys.Asn.Gln.Gln.Asp.Phe.Pro

6. H2N-Lys.Ser.Pro.Cys.Ala.Tyr.Lys.Glu.
|
Pro
.
HO-Cys.Ala.Val.Thr.Thr.Glu

FIG. 1

P-OH + $(CH_2CO)_2O$ $\xrightarrow[\text{Pyridine, 50°}]{\text{Anhyd}}$ P-O-CO-$(CH_2)_2$-COOH
1

FIG. 2A

XHN-Pept-Resin $\xrightarrow[\text{of } \alpha\text{-NH2}]{\text{Deprotection}}$ $H_2N$-Pept-Resin
2

P-O-CO-$(CH_2)_2$-COOH + $H_2N$-Pept-Resin $\xrightarrow{\text{DCC or DIPC}}$

P-O-CO-$(CH_2)_2$-CO-HN-Pept-Resin $\xrightarrow{\text{Cleavage}}$

P-O-CO-$(CH_2)_2$-CO-NH-Pept-COOH
3

P = tolerogenic polymer (mPEG or PVA)
DCC = dicyclohexylcarbodiimide
DIPC = diisopropylcarbodiimide
X = t-Boc or Fmoc

FIG. 2B

PVA OR PEG CONJUGATES OF PEPTIDES FOR EPITOPE-SPECIFIC IMMUNOSUPPRESSION

CROSS-REFERENCE TO RELATED APPLICATIONS

This application is a continuation of Ser. No. 07/811,050 filed Dec. 19, 1991 (abandoned).

This invention was made, at least in part, with government support under Grant No. NS26280 awarded by the National Institutes of Health. The government may have certain rights in the invention.

BACKGROUND OF THE INVENTION

A. Field of the Invention

The invention relates, in one aspect, to a procedure for synthesis of well-defined conjugates of peptides covalently bonded to a tolerogenic polymer such as monomethoxypolyethylene glycol (MPEG) or polyvinyl alcohol (PVA). The first step in said synthesis involves succinylation of free-hydroxyl groups on the tolerogenic polymer by reaction with succinic anhydride. The polymer is then coupled to one or the other terminus, for instance via the carboxyl of a succinyl group to the α-$NH_2$, of a peptide. This is achieved while maintaining intact all the side-chain protecting groups on the peptide. The MPEG or PVA-peptide conjugate are cleaved from a synthetic resin and purified. This method results in the preparation of conjugates in which one molecule of tolerogenic polymer is specifically coupled to one or the other or both of the termini of an otherwise unaltered peptide molecule.

In order to test the ability of such tolerogenic peptides to suppress antibody responses in an autoimmune disease, a synthetic peptide, α125–148, corresponding to a myasthenogenic region of *Torpedo californica* acetylcholine receptor (AChR) was conjugated to monomethoxypolyethylene glycol (MPEG). Injection of mice with the MPEG-(α125–148) conjugate and subsequent immunization with whole Torpedo AChR suppressed the development of experimental autoimmune myasthenia gravis (EAMG) by electrophysiological criteria. In anti-AChR antisera from these animals, the antibody response against the unconjugated peptide α125–148 was decreased while the antibody responses against whole AChR and other epitopes were not altered. There were no detectable changes in T cell proliferation responses to peptide α125–148 or to whole AChR in these animals. Prior injections with a "nonsense" peptide mPEG conjugate had no effect on responses to the subsequent immunization with whole Torpedo AChR. The results indicate that the mPEG-(α125–148) conjugate has epitope-specific tolerogenicity for antibody responses in EAMG, and that the region α125–148 plays an important pathophysiological role in EAMG. These studies strongly indicate that other epitope-directed tolerogenic conjugates will be useful for future immunotherapies of human myasthenia gravis.

Tolerogenic peptides are also disclosed for diseases as diverse as ragweed pollen allergy and Grave's disease. The strategy of specific suppression of the antibody response to a pre-determined epitope using a synthetic mPEG-peptide conjugate will be useful in manipulation and suppression of unwanted immune responses such as autoimmunity and allergy.

B. Description of the Related Art

Some of the earliest methods combining the use of amino acid synthesis with polymers such as polyethylene glycol (PEG) were as a resin for the synthesis of peptides. These methods relate generally to attachment of PEG at the carboxy terminus of the growing peptide chain. Typically, the resulting synthetic peptide is ultimately cleaved from the PEG resin and purified. For instance, Anzinger and Mutter (1982), relates to modified PEG moieties capable of binding both C- and N-termini of synthetic peptides for purposes as a soluble carrier and as a solubilizing protecting group in peptide syntheses.

Alternatively, tolerogenic polymers have been used to derivatize proteins and peptides in a permanent, covalent fashion. Prior research has shown that mPEG-protein conjugates may be constructed by non-selective coupling of the polymer to proteins, usually via the e-amino groups of lysine residues on the surfaces of such proteins. Such substitutions result in multiple derivatives.

Previous studies, for instance, have shown that conjugation of polyethylene glycol, monomethoxypolyethylene glycol (MPEG: or polyvinyl alcohol (PVA) with various protein antigens causes a loss of most of the antigenicity of the native antigens (Abuchowski et al., 1977; Lee and Sehon 1977, 1978a; King et al., 1977, 1979; Davis et al., 1980; Sehon and Lang, 1986). It has also been demonstrated that prior injection of animals with antigen-mPEG conjugates leads to the development of tolerance to subsequent immunization with the native antigen (Lee and Sehon 1977, 1978b; King et al., 1979).

mPEG-derivatization has been used to produce whole-protein and protein fraction conjugates. Abuchowski et al. (1977) relates, for instance to the derivatization of bovine serum albumin with mPEG causing this molecule to become essentially non-immunogenic. Lee and Sehon (1977) similarly converted ovalbumin and mixtures of non-dialyzable allergenic constituents of the aqueous extract of ragweed pollen. King et al. (1979) relates to the comparative study of different tolerogenic polymers indiscriminately conjugated with ragweed antigen E. Nishimura, et al. (1983), relates to the use of an indiscriminately PEG-derivatized snake venom with a molecular weight of 36,000. British Patent 1 469 472 appears to relate to the desire to provide polypeptides such as insulin a longer residence time in the circulatory system and a lessened allergic reaction in the same by apparently indiscriminate conjugation of such polypeptides to PEG.

In certain cases, the indiscriminate conjugation of polymer to protein has been controlled to a limited extent. For instance, European Patent Application 0 335 423 relates to the hG-CSF polypeptide derivatized with a PEG moiety. The derivatization appears to be indiscriminate even though the disclosure does provide for as few as a single PEG molecule per molecule of hG-CSF by controlling the stoichiometric ratios of the polymer to protein. Kita, et al. (1990), relates to the selective modification of one of three (including the N-terminal) residues within human interferon in order to obtain active interferon from recombinant bacteria. The PEG modification was seen to increase the serum half-life of the interferon without substantial decrease in its biological efficacy.

Tolerogenic polymers have also been used to derivatize certain peptides. In the past, modifying peptides with PEG generally required use of methods for activation including: (1) activation with triazine derivatives of PEG; (2) activation of PEG using the active ester method with N-hydroxylsuccinimide; (3) activation of PEG with carbonyldiimidazole; (4) activation of PEG with aldehydes; and so on. These modification methods involve modifying the amino groups at the N-terminal or in the side chain of the lysine residues of the peptides. For instance, Becker and Bayer (1979), relates to synthetic peptides with PEG conjugated to $NH_2$ groups which are available for coupling. In certain cases, where the only reactive $NH_2$ group in the peptide is the $\alpha$-$NH_2$, the PEG molecule was conjugated to the N-terminus of the peptide. Such methodology, however, relied on the fact that no other reactive amine groups existed in the peptide to be derivatized.

In some instances, peptides have been derivatized using distinct chemical moieties apart from the N-terminus amino group. Ueyama, et al. (1985), relates to the conjugation of PEG to cysteine-containing peptides through the carboxy groups in said cysteines. European Patent Applications 0 340 741 and 0 400 486 relate to PEG derivatives for use as a peptide (particularly protein)-modifying reagent in peptides having guanidino groups. PCT International Application, Pub. No. 90/12874, relates to the modification of polypeptides such as IL, G-CSF or EPO by non-N-terminal conjugation of PEG to cysteine residues in such polypeptides. Sartore, et al. (1991), relates to a method of producing a reagent comprising mPEG attached to an amino acid or a peptide, the amino acid or peptide functioning as a traceable spacer arm between the reagent and a derivatizable polypeptide in order to change its immunological properties. The attachment of the mPEG polymer to the peptide was at the carboxy terminus leaving, apparently, a free reactive amine functional group at the other terminus.

It is known, however, that heterogenous mixtures of "PEGylated" polypeptides and peptides are unsuited for pharmacological purposes (see e.g., PCT International Application, Pub. No. 90/12874). Indiscriminately conjugated proteins and peptides will, almost invariably, be expected to contain a mixture of molecular species or derivatives.

The use of tolerogenic antigens, alloantigens and allergens has received recent interest from the medical community for the treatment of autoimmune type disease. Typically, as noted above, the methods of the prior art utilize randomly derivatized whole antigen. Certain models of these diseases are known, however, which may serve as a testing ground for new approaches.

For instance, animals immunized with acetylcholine receptors (AChRs) in the presence of complete Freund's adjuvant produce autoantibodies against AChRs and develop a neuromuscular disease similar to human myasthenia gravis. In this experimental animal disease, called experimental autoimmune myasthenia gravis (EAMG), the majority of the autoantibodies is directed against the main extracellular part of the a subunit of AChR. The mapping of the complete antibody recognition profile, using overlapping synthetic peptides representing the entire extracellular part of the $\alpha$ subunit of *Torpedo californica* AChR, demonstrated that the peptide $\alpha$125–138 contains a major antigenic site (Mulac-Jericevic et al., 1987). This epitope is located within the sequence $\alpha$125–148 which is a potent region for induction of EAMG (Lennon et al., 1985) and contains the acetylcholine binding site (McCormick and Atassi 1984).

Other autoimmune diseases and other undesirable immune responses such as allergic responses have been investigated sufficiently well to identify similar specific epitopes which may be the principal causative agent in the disease. Thus, for instance, ragweed pollen allergy is a condition resulting from IgE responses to ragweed allergens such as antigen E, antigen K and Ra3. Thus, it is known from the work of the present inventors that one can map the IgG and IgE antibody and the T-cell epitopes of Ra3 (Atassi and Atassi, 1985, 1986; Kurasaki et al. 1986). Animal models (rat) exist which are used to study the allergic responses.

Similarly, Grave's disease is an autoimmune disease caused by antibody and T-cell responses to epitopes on thyroid-stimulating receptor (TSHR). Recently, the hormone-binding regions on TSHR were localized (Atassi, et al. 1991). As is known due to recent press coverage, both human (President and Mrs. George Bush) and animal (the family pet dog of the President and First Lady) forms of this disease are known.

Where mixtures of indiscriminately derivatized peptides; such as the specific epitopes described above are used as tolerogens, problems associated with reproducibility and efficacy are common. In particular, in cases where autoimmune disease are the result of limited specific epitopes being the target of the autoimmune antibodies, tolerogenic mixtures are not desirable. What are needed are specifically-derivatized, epitope-specific conjugated peptides.

SUMMARY OF THE INVENTION

The present invention overcomes at least some of the problems existing in prior art approaches to the construction of reagents for the treatment of autoimmune diseases. In one aspect, the invention broadly discloses a synthetic method for construction of specifically-modified peptides covalently attached to a polymer which renders the synthetic peptide tolerogenic. In another aspect, the invention broadly discloses the use of these specifically-modified synthetic peptides in the treatment of diseases of autoimmunity and other unwanted responses such as allergic reactions and graft rejections. In yet another aspect, the invention provides for the reagents designed to immunosuppress undesirable immune responses. The invention also provides a method of testing such reagents for efficacy as immunosuppressants.

More specifically, a method of producing reagents useful in the treatment of autoimmune diseases is disclosed herein. In certain preferred aspects, the method for producing such reagents entails producing a peptide covalently linked via its carboxy-terminal amino acid to a synthetic resin. It will be understood well by those of skill in the art, however, that due to its ease, coupling of the carboxy terminus to the synthetic resin is only one manner in which to provide a single free, amino terminus for subsequent derivatization. However, the same skilled artisan will also realize that it is possible to use alternative protocols to specifically block the amino terminus and to derivatize the carboxy terminus of such a peptide. Therefore while the preferred technique will involve a carboxy terminus attached to a synthetic resin and a free amino terminus, derivatization of either or both termini is anticipated by the inventors to give equally efficient tolerogenic peptides.

Any of the synthetic resins known to those of skill in the art will be amenable to the methodology. For instance, one may use synthetic methods based on either t-butyloxycarbonyl (t-Boc) derivatized amino acids synthesized on a phenylacetamidomethyl (PAM) resin or by 9-fluorenmethylcarbonyl (Fmoc) derivatized amino acids on a benzyloxybenzyl alcohol resin (McCormick and Atassi 1984; Mulac-Jericevic and Atassi, 1987; Atassi et al., 1991).

The peptides of the invention will typically be protected from inadvertent coupling along the side chains by the presence of side chain-protected amino acids in the peptide. It will be well understood by those of skill in the art that such side chain protecting groups can vary depending upon the nature of the synthetic procedure.

In the preferred embodiment, the peptide may be synthesized beginning with any sized initial peptide fragment attached by its carboxy terminus to the resin. Thus, it will be understood by those of skill in the art that one may obtain presynthesized and derivatized peptides of variable lengths. Alternatively, one may obtain from any number of commercial sources synthetic resins which have one or more derivatized amino acids coupled to the resin by its carboxy terminus. The invention, therefore, is not limited to the use of wholly synthetic peptides and may include peptide fragments derived from native antigens themselves or from antigens obtained using recombinant DNA technology so long as these peptides may be protected along their side chains and covalently bound to a resin at their carboxy or amino terminus.

The peptides produced by the methods of the invention will typically correspond to an epitope which is suspected of inducing an autoimmune response or other undesired responses such as allergic conditions or graft rejections. Such an epitope may be suspected for any number of reasons. There may be empirical data which indicate a specific and relatively restricted epitope as a linear sequence found as an identical sequence in the native antigen known to cause the immune response of the disease. Alternatively, such an epitope may be a non-linear sequence corresponding to an antigenic region of a native antigen but which linear sequence does not exist as such in the native antigen.

Moreover, the peptides produced by the invention may be suspected as epitopes due to a regional localization to a region known to contain the minimally-sized epitope inducing the maximal antigenic response in the immune disease. For instance, it is known by those of skill in the art that many cell membrane-associated antigens chiefly present the extracellular portions of the polypeptide as potential epitopes. Thus, the epitope suspected of inducing the immune response may only be suspected as a battery of potential epitopes which are typically presented in the physiological state. In some cases, therefore, one may wish to test a battery of overlapping peptides representing sequential segments of the exposed extracellular regions of a given native antigen.

The peptide so selected and/or synthesized is attached to a resin by one of its termini, preferably by its carboxy-terminus, and is then derivatized at its other, preferably amino, terminal amino acid with a tolerogenic polymer. Since all side chains will still be protected as they were during the synthetic procedure, and since one terminus is likewise protected by coupling to the resin, the only reactive group will occur at the other terminus, preferably at the growing N-terminal amino acid as the $\alpha$-$NH_2$ of that terminal residue. It is to this terminus that the tolerogenic polymer is attached.

The methods of the invention complete the synthesis of the terminally protected, tolerogenic peptides by deprotecting the side chain-protected amino acids comprising the peptide. Depending on the nature of the synthetic chemistry used to construct the peptide, deprotection will be achieved variously by methods known well to those of skill in the art. Similarly, depending upon the resin used to initiate synthesis, cleaving the peptide from the resin will take various forms. Purification of the peptide will also take various forms depending upon the nature of the resulting peptide. In some cases, more hydrophilic peptides may be amenable to purification schemes depending upon the solubility of the peptide in water based solvents. More hydrophobic peptides may require organic solvents and purification schemes in which the peptides will be most soluble.

Even though methods of the invention relate to any epitope-specific tolerogenic peptide used to construct reagents capable of treating immune diseases, the invention relates more specifically to certain characterized peptide reagents. Thus, the invention discloses the specific construction of any of the peptides shown in Sequence ID Nos. 1–7. Certain of these specific peptide reagents relate to specific immune diseases such as myasthenia gravis, ragweed pollen allergy, and Grave's disease. Moreover, the methods of the invention relate to specific native polypeptides such as a subunit of an acetylcholine receptor, ragweed pollen antigen Ra3, or a polypeptide subunit of the thyroid-stimulating hormone receptor responsible for Grave's disease.

It is preferred that the peptide reagent designed will be directly or indirectly responsible for the major immune response as the principal causative agent of symptoms of the immune disease. However, there may be instances where peptides corresponding to regions of the native antigen responsible for lesser immune responses will be desired. In particular, combinations of reagents, each of which accounts in part for the immune response, may be preferred in certain instances.

The methods of the invention require the covalent coupling of a tolerogenic polymer to the peptide reagents. Such tolerogenic polymers are known well to those of skill in the art. For instance, such a polymer may be polyethylene glycol or a polyethylene glycol derivative. In a preferred embodiment of the invention, the monomethoxy derivative of polyethylene glycol will be used. Alternatively, polyvinyl alcohol or a derivative of polyvinyl alcohol may be used.

In any instance, the basic polymer selected will be treated in a manner as to make the polymer amenable to a coupling reaction. In a preferred embodiment, the method used to derivatize the polymer will involve succinylation of the polymer so as to derivatize the hydroxyl groups of the polymer and to generate any number of reactive carboxyl groups. Complete derivatization is monitored as is availability of the reactive carboxy groups on the surface of the modified polymer.

In another principal aspect of the invention, a method of treating an autoimmune disease is disclosed. The method consists of first producing a tolerogenic polymer-derivatized peptide as described above. The peptide reagent so produced will typically correspond to an epitope which is suspected of inducing an autoimmune response of the disease. After the peptide is so produced, the method treats a patient with the peptide. The patient may be one who has the disease. Alternatively, the patient may be one who is likely to develop the autoimmune disease. For instance, certain autoimmune diseases have long non-symptomatic episodes in which major immune responses are not present. In the autoimmune disease myasthenia gravis, patients typically experience sometimes very lengthy non-symptomatic periods followed by periods of almost complete debilitation due to the ongoing immune response. The patient is thus treated at an optimal time with tolerogenic peptide, preferably prior to onset of a major autoimmune response to the natural antigen from which the epitope was designed.

Reagents useful in the treatment of an autoimmune disease are also disclosed in the present invention. Generally, such a reagent will be a peptide corresponding to an epitope which is suspected of inducing an autoimmune response which peptide is derivatized at an N-terminal amino acid of the peptide with a tolerogenic polymer.

More specifically, the reagent will be one of the group of peptides disclosed in Sequence ID Nos. 1–7. It will be recognized, however, by those of skill in the art that the reagent peptides may contain functionally equivalent amino acid substitutions. The importance of the hydropathic index of amino acids in conferring biological function on a protein has been discussed generally by Kyte and Doolittle (1982). It has been found by these researchers and others that certain amino acids may be substituted for other amino acids having a similar hydropathic index or score and still retain similar if not identical biological activity. As displayed in Table I below, amino acids are assigned a hydropathic index on the basis of their hydrophobicity and charge characteristics. It is believed that the relative hydropathic character of the amino acid determines the secondary structure of the resultant protein, which in turn defines the interaction of the protein with the substrate molecule. Similarly, in peptides whose secondary structure is not a principal aspect of the interaction of the peptide, position within the peptide and the characteristic of the amino acid residue determine the interactions the peptide has in a biological system. It is proposed that biological functional equivalence may typically be maintained where amino acids having no more than a +/−1 to 2 difference in the index value, and more preferably within a +/−1 difference, are exchanged.

TABLE I

| | HYDROPATHIC INDEX |
|---|---|
| Isoleucine | 4.5 |
| Valine | 4.2 |
| Leucine | 3.8 |
| Phenylalanine | 2.8 |
| Cysteine/Cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, can be substituted for valine (+4.2) or leucine (+3.8), and still obtain a protein having similar biologic activity. Alternatively, at the other end of the scale, lysine (−3.9) can be substituted for arginine (−4.5), and so on.

Accordingly, these amino acid substitutions are generally based on the relative similarity of R-group substituents, for example, in terms of size, electrophilic character, charge, and the like. In general, although these are not the only such substitutions, the preferred substitutions which take various of the foregoing characteristics into consideration include the following:

TABLE II

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala |

TABLE II-continued

| Original Residue | Exemplary Substitutions |
|---|---|
| His | asn; gln |
| Ile | leu; val |
| Leu | ile; val |
| Lys | arg; gln; glu |
| Met | met; leu; tyr |
| Ser | thr |
| Thr | ser |
| Trp | tyr |
| Tyr | trp; phe |
| Val | ile; leu |

More particularly, the invention relates to a method of producing reagents useful in the treatment of myasthenia gravis. In such a method, a peptide is synthesized corresponding to the peptide shown in Sequence ID No. 5. This peptide is covalently linked during and after synthesis to a carboxy-terminal amino acid of the peptide to a resin and possesses side chain-protected amino acids. As is described in more detail below, this peptide corresponds to an epitope which is suspected of inducing a myasthenia gravis autoimmune response. The peptide is then derivatized at an N-terminal amino acid of said peptide with mPEG. Following derivatization with the tolerogenic polymer, the reagent is deprotected along its the side chain-protected amino acids, cleaved from the resin, and purified. Even though such a specific reagent is disclosed, it will be understood that other myasthenogenic peptides will be amenable to the general methods of the invention in order to produce suitable reagents for treatment of the disease alone or in combination with other drugs and treatments.

A similar method is disclosed relating to production of reagents useful in the treatment of ragweed allergy. In the case of the specific ragweed peptide disclosed herein, the peptide will correspond to the peptides shown in Sequence ID Nos. 1–4. Similarly, a method of producing reagents useful in the treatment of Grave's disease are disclosed herein. Reagents produced by any of the methods of the invention as they relate to Grave's disease are also disclosed (See, Atassi et al. *Proc. Ntl. Acad. Sci USA* 88:3613–3617 [1991], specifically incorporated by reference herein).

As regards specific methods of treating specific immune diseases, the invention discloses methods for treating myasthenia gravis, ragweed allergy, and Grave's disease. In certain preferred embodiments, these methods will more particularly utilize an mPEG-derivatized peptide corresponding to those peptides identified in Sequence ID Nos. 1–7.

In another major aspect of the invention, methods of screening reagents potentially useful in the treatment of autoimmune diseases is disclosed. In a general application of this method, one produces a peptide covalently linked via one of its terminal ends, such as the N-terminal amino acid, of the peptide to a resin such as those disclosed below, protecting the amino acid residues accordingly with side chain-protecting groups. The candidate peptide will typically correspond to an epitope or an amino acid sequence from a region believed to contain such an epitope, which is suspected of inducing an autoimmune response. The candidate reagent will be completed by derivatizing the N-terminal α-$NH_2$ (or the C-terminal carboxyl) of the peptide with a tolerogenic polymer, deprotecting the side chain-protected amino acids comprising the peptide, cleaving the peptide from the resin, and purifying the peptide.

As a next step in the screening method, a test subject having, or likely to develop, the immune (such as an autoimmune) disease or an experimental model of the immune disease is treated with the peptide reagent. The treatment will preferably occur prior to onset of an immune response to an autoantigen (or allergen) or transplantation antigen) comprising the epitope. Finally, the test subject will be evaluated for alleviation of symptoms related to said immune response.

It will be understood by those of skill in the art that the method of screening generally outlined above will typically be applied where the peptide under investigation is one of a battery of peptides whose sequences are derived in some manner from the native protein suspected of causing the immune response. Methods of treatment of the test subject may vary according to the nature of the reagent or the strictures of the testing protocols, but typically will involve the injection of the peptide reagent into the test subject at selected intervals and without an adjuvant.

A method of screening reagents potentially useful in the treatment of myasthenia gravis, is described, for instance, which involves producing peptides using the methods described herein based upon the extracellularly accessible regions of certain polypeptide subunits of the acetylcholine receptor. The test subject is then treated with the tolerogen-peptide conjugate. The test subject may be a human test subject having, or likely to develop, myasthenia gravis. Alternatively, and in a preferred embodiment where experimental drugs are first screened, the test subject may be a non-human animal such as a mouse in which experimental autoimmune myasthenia gravis has been induced using injections of the native antigen, acetylcholine receptor derived from the Torpedo. As described previously, one wishing to use such a screening method will typically time the treatments of the test subject with the peptide reagent prior to onset of an autoimmune response to an acetylcholine receptor polypeptide. The test subject following treatment will be evaluated for alleviation of symptoms related to myasthenia gravis or an experimentally induced model thereof. Where possible, evaluation of the test subject for alleviation of symptoms further comprises evaluating the test subject using electrophysiological criteria.

BRIEF DESCRIPTION OF THE DRAWINGS

FIG. 1. Covalent structure of the synthetic peptides used in the present work for coupling to mPEG and to PVA. Peptide 1 was synthesized on a PAM-resin by t-Boc amino acids as described earlier (from McCormick and Atassi, 1984). Peptides 2–6 were synthesized on a benzyloxybenzyl alcohol resin by Fmoc amino acids.

FIG. 2. Scheme for synthesis of mPEG-peptide and PVA-peptide conjugates. In step A, the aliphatic hydroxyl groups on mPEG and PVA are reacted with succinic anhydride. In step B, the synthetic peptide, while still on the resin with all the side-chain protecting groups intact, is deprotected at the α-$NH_2$ group only (compound 2) and then coupled through this now free amino group to the carboxyl group of compound 1 using a carbodiimide and an excess of compound 1. Complete blocking of the amino group is monitored and recoupling is performed if necessary. When free amino groups are no longer detectable, the peptide is cleaved from the resin. This scheme is a general procedure for the synthesis of mPEG-peptide and PVA-peptide conjugates (compound 3). The peptide conjugate is then lyophilized and subjected to purification.

DESCRIPTION OF PREFERRED EMBODIMENTS

Figure 3:
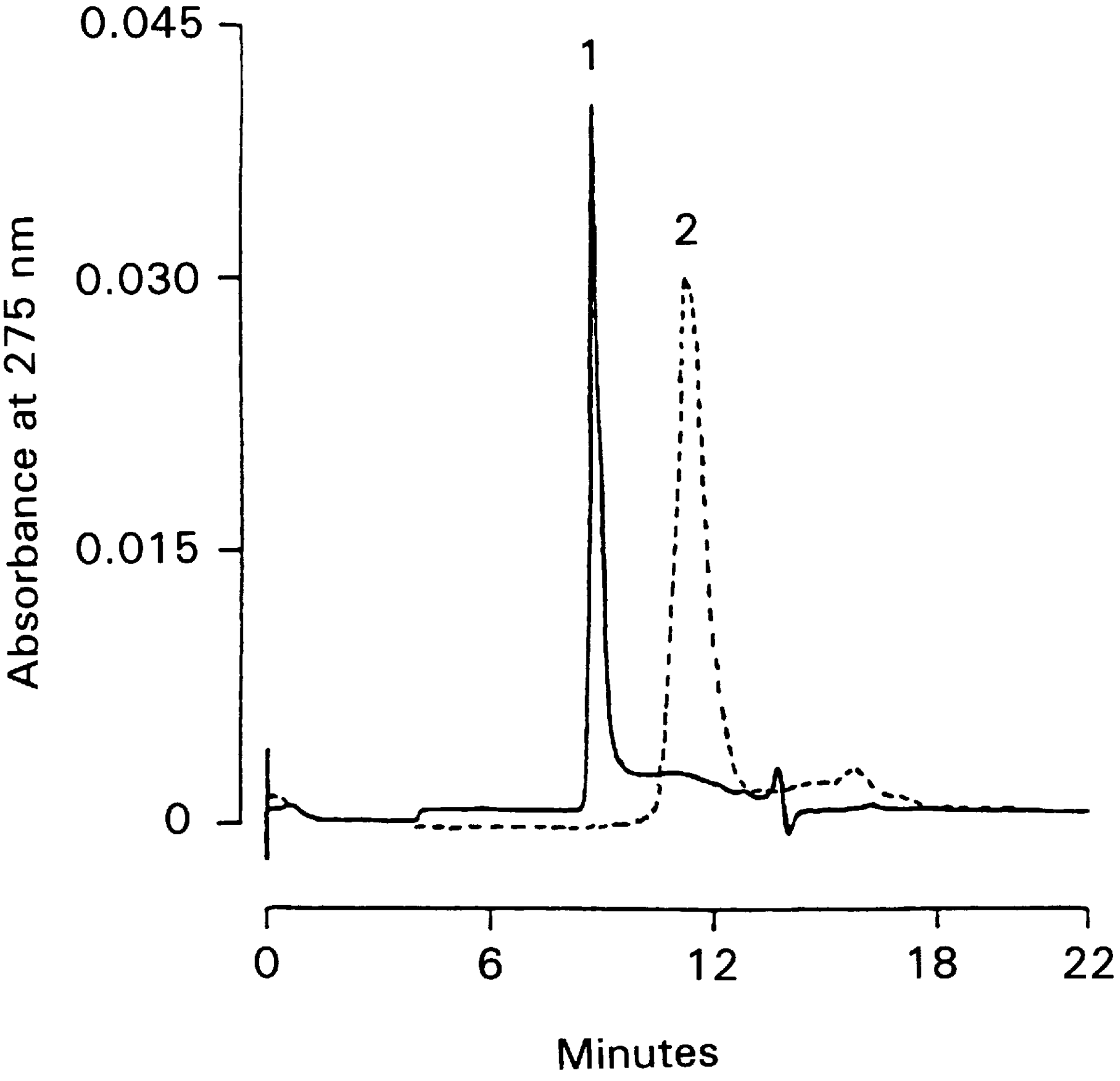
FIG. 3. An example of elution profiles of (1) the parent unconjugated peptide (peptide 5, FIG. 1) and (2) an mPEG-peptide conjugate in HPLC on a size exclusion column (Waters Protein Pak 60, 0.7×30 cm). The column was eluted with 0.2 M ammonium bicarbonate containing 20% acetonitrile at 0.70 ml/min.

In general aspects, certain protocols and procedures will be applicable to the various methods and compositions of matter of the invention. These general techniques are detailed below.

Peptide Synthesis and Purification

The peptides used for certain particular examples of the invention are shown in FIG. 1 and correspond to the Sequence ID Nos. 1–6. These peptides, as well as other peptides produced using the methods of the invention, are synthesized either by t-butyloxycarbonyl (t-Boc) on a phenylacetamidomethyl (PAM) resin or by 9-fluorenmethylcarbonyl (Fmoc) amino acids on a benzyloxybenzyl alcohol resin as described elsewhere (McCormick and Atassi 1984; Mulac-Jericevic and Atassi, 1987; Atassi et al., 1991), together with methods for purification and characterization of the peptides.

Buccinylation of the hydroxyl groups of mPEG and PVA

To prepare the succinate esters of mPEG and PVA, one gram of mPEG (molecular weight, 5000) or PVA (molecular weight 3,000) is dissolved in 5 ml anhydrous pyridine at 50° C., and to these solutions aliquots of succinic anhydride (0.5 g each) are added as a dry powder at 1-hour intervals. Following the last addition, the reaction mixture is stirred for 2 hours at 50° C., after which it is evaporated to dryness on the flash evaporator. The residue is dissolved in water and evaporated to dryness and this washing with water on the evaporator is repeated several times until the odor of pyridine in the residue is very faint. The residue is dissolved in water (10 ml) and dialyzed, in a 1000-molecular weight cut-off dialysis membrane, against several changes of distilled water and finally freeze-dried (yield 0.92–0.95 g). Complete succinylation of the polymers is confirmed by a negative reaction for hydroxyl and a positive reaction for carboxyl groups.

Determination of hydroxyl and carboxyl groups in the polymers

Determination of hydroxyl groups is carried out by a modification of the procedure described by Siegelman et al. (1962). A solution of test sample (365 μl containing 2 mg of MPEG, PVA mPEG-Su, PVA-SU, succinic anhydride, and standards containing various amounts of methanol from 0 to 1.5 μmole in 0.06 M sodium phosphate buffer pH 7.5, containing 0.09 M NaCl, is mixed with 182 μl of 0.75 M perchloric acid. A blank is prepared which contains the same reagents but without a test sample. After mixing, the tubes are centrifuged (2000 rpm, 20 min.) and 365 μl aliquots from each tube are transferred to clean test tubes. To each tube is added 40 μl of 2% $KMnO_4$ (in water), the solutions are mixed for exactly 1 minute, then 40 μl of freshly prepared 10% sodium sulfite (in water) is added and the tubes are immediately shaken vigorously. At this point, the solutions should become completely decolorized. To these solutions is added 1.45 ml of chromotropic acid reagent [8 mg of 4,5-dihydroxy-2,7-naphthalene-disulfonic acid disodium salt (Sigma Chemical Co., St. Louis, MO) dissolved in 0.10 ml $H_2O$ and 1.35 ml sulfuric acid solution (Conc. $H_2SO_4$/water, 2:1, v/v)]. The tubes are covered and placed in boiling water for 15 min. after which they are cooled to room temperature and the absorbance of the solutions is read at 580 nm against the blank solutions in the reference cell. The hydroxyl group content of a sample is determined based on the methanol standard curve of absorbance versus amount of methanol ($A^{1cm}_{580}$ for 1μ mole of $CH_3OH$=0.856).

Carboxyl groups are detected by the method described by Brown (1951). An aliquot of a water solution of the test sample (20 μl containing 1 mg of mPEG, PVA mPEG-Su or PVA-SU) is applied as a spot on Whatman No. 3MM Chr paper. The spot is dried with cold air and the paper is then stained by spraying with a solution of 0.04% bromothymol blue in ethanol, preadjusted to pH 8.0 with 0.2 M boric acid. mPEG-Su and PVA-Su give bright yellow spots on a blue background, whereas the spots of mPEG and PVA appear blue.

Coupling of mPEG or PVA succinates to synthetic peptides

A coupling method for the preparation of mPEG-peptide and PVA-peptide conjugates is illustrated in FIG. 2. The synthesis resin (0.1 g) carrying the completed synthetic peptide (0.025 m mole), with all the side chain protecting groups intact, is swollen in a synthesis vessel in methylene chloride overnight. The t-Bloc protecting group on the a-amino group of the synthetic peptide is removed by treatment with 40% trifluoroacetic acid containing 2% anisole and 2% dimethylformamide (DMF) at room temperature for 30 minutes. For the Fmoc-peptides, the $N^{\alpha}$-Fmoc protecting group is removed by 20% piperidine in DMF. For coupling of mPEG-Su, a three-molar excess in 1.5 ml of DMF is reacted with 0.2 ml of 50% dicyclohexylcarbodiimide (DCC) or diisopropylcarbodiiniide (DIPC) in methylene chloride for 20 minutes, filtered to remove dicyclohexyl urea (if DCC is used), then added to the N-terminal-deprotected peptide-resin and allowed to react for 24 hours. For coupling of PVA-Su, larger reaction volumes are needed because of its tendency to gel. Three-molar excess of PVA-Su is dissolved in 8.0 ml of DMF and to this is added 0.20 ml of 50% DCC or DIPC in methylene chloride. Three cycles of recoupling of mPEG-Su or PVA-Su to the peptide-resin are done. The complete blocking of the α-$NH_2$ is confirmed by a ninhydrin test (Kaiser et al, 1970). After the a-amino group on the peptide is completely blocked, uncoupled mPEG-Su or PVA-Su is washed out of the vessel with methylene chloride and then methanol. The peptide conjugate is cleaved from the resin by HF (Sakakibara et al, 1967), if a PAM resin and t-Boc amino acids are used, or by treatment (2.5 hr) with 55% trifluoroacetic acid in methylene chloride if a benzyloxybenzyl alcohol resin and Fmoc amino acids are used.

Any residual uncoupled peptide is removed from the conjugate by gel filtration on a Sephadex G-75 fine column (1.5×75 cm) in 0.1 M ammonium bicarbonate and by high pressure liquid chromatography (HPLC) on a size exclusion column (Waters protein pack 60, 0.7×30 cm) which is eluted with 0.2 M ammonium bicarbonate containing 20% acetonitrile at a flow rate of 0.7 ml/min.

Preparation of Torpedo AChR

The purification of Torpedo AChR is carried out as described elsewhere (Froehner, 1979; Mulac-Jericevic and Atassi, 1987). Briefly, the electric organ of *Torpedo californica* (Pacific Bio-Marine Laboratories, CA) is homogenized and the membrane proteins are extracted in 1% Triton X-100 (Sigma Chemical Company, MO). After centrifugation, the AChR in the supernatant is affinity purified on a cobratoxin Sepharose CL4B column using 1M carbamylcholine in 1% octyl β-D-glucopyranoside (Sigma Chemical Company, MO) for the elution of the AChR. The purified AChR is composed of the expected four subunits (α, β, γ, δ) as demonstrated by SDS-PAGE (Laemmli, 1970).

Synthesis of Myasthenic Peptides and their mPEG conjugates

The structure of peptide α125–148 (FIG. 1, No. 5) of Torpedo AChR was based on the amino acid sequence of the extracellular part of the receptor (Noda et al., 1982). The peptide was synthesized and purified as described by McCormick and Atassi (1984). Cyclization of the synthetic peptide α125–148 was performed under conditions previously described (McCormick and Atassi, 1984). The monomeric form was separated by gel filtration on Sephadex G-25 fine (Pharmacia Fine Chemicals) column in 0.1 M ammonium bicarbonate. After purification, homogeneity of the monomeric peptide was confirmed by high-voltage paper electrophoresis (Atassi and Saplin 1968). The amino acid composition of the peptide was in excellent agreement with that expected from its sequence. A nonsense peptide, having a structure (HFKSFHSFSVSGETVFEVTEAG) totally unrelated to AChR, was also synthesized and employed as a negative control.

The coupling method for the preparation of mPEG-peptide conjugates is described above and in Atassi and Manshouri (1992).

Figure 4:
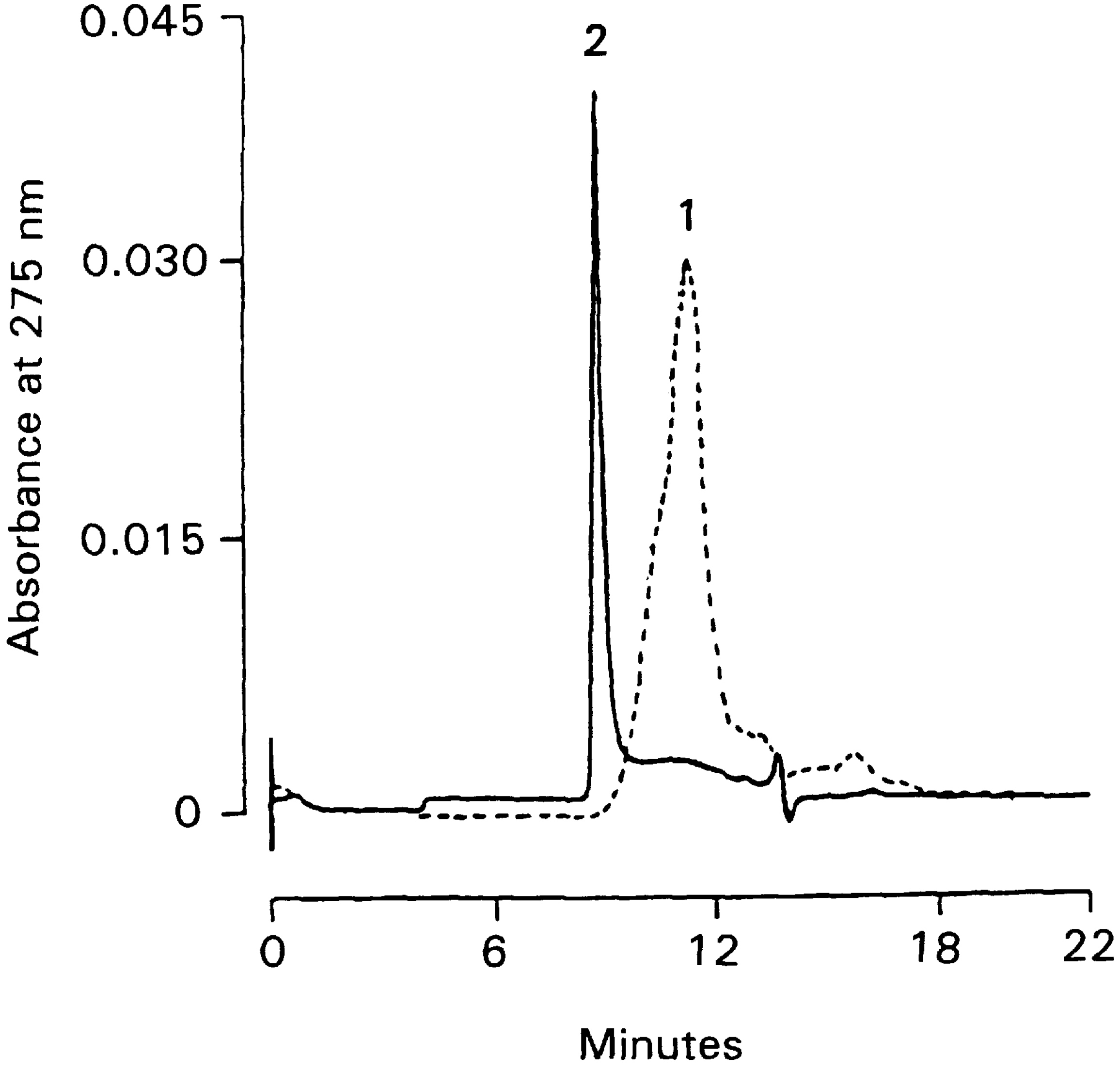
FIG. 4. Elution profiles of: (1) peptide α125–148, and (2) mPEG-(α125–148) conjugate in HPLC on a size exclusion column (Waters protein pak 60, 0.7×30 cm). The column was eluted with 0.2 M ammonium bicarbonate containing 20% acetonitrile at 0.70 ml/min.

After synthesis of the conjugates and cleavage from the synthesis resin, any residual uncoupled peptide was removed from the conjugate by gel filtration on a column (1.5×75 cm) of Sephadex G-75 fine in 0.1 M ammonium bicarbonate. After lyophilization, the mPEG-(α125–148) conjugate was cyclized and the monomeric species isolated as described (McCormick and Atassi, 1984). A sample of the purified peptide-mPEG conjugate was confirmed to be free of the uncoupled peptide by high performance liquid chromatography (HPLC) on a size exclusion column (Waters protein pack 60, 0.7×30 cm) which was eluted with 0.2M ammonium bicarbonate containing 20% acetonitrile at a flow rate of 0.7 ml/min (FIG. 4).

Tolerization and Immunization

Figure 5:
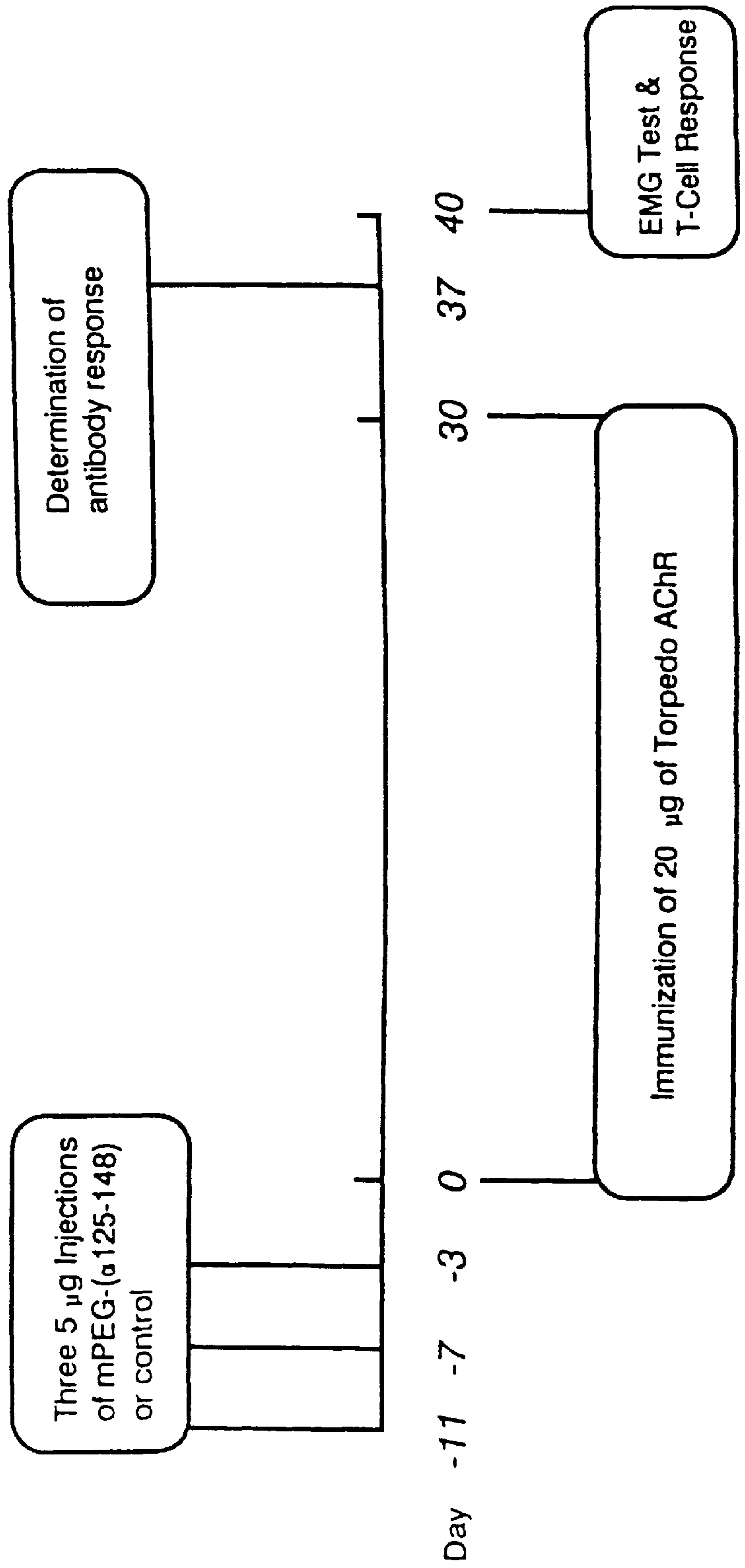
FIG. 5. Protocol for the intraperitoneal injections of C57/BL6 mice with mPEG-peptide conjugates (or the unconjugated peptide) and subsequent immunizations with whole Torpedo AChR.

Six weeks old C57/BL6 mice were purchased from Charles River Breeding Laboratories (Wilmington, Mass.). Preimmune sera were obtained from the mice for use as controls in subsequent antibody binding assays. After 2-weeks rest, the mice were divided into three groups which received, at eleven, seven and three days before immunization with AChR, an intraperitoneal injection (5 μg in 25 μl of PBS) of either the mPEG-(α125–148) conjugate (Group 1), mPEG-nonsense peptide conjugate (Group 2) or unaltered free peptide α125–148 (Group 3) (FIG. 5). Then, on day 0, the mice were immunized subcutaneously in one hind footpad and intramuscularly in the same side shoulder with 20 μg of Torpedo AChR in 100 μl emulsion containing equal volumes of complete Freund's adjuvant and PBS. Thirty days later, the mice were immunized with a similar dose of the receptor in the opposite footpad and shoulder. On the 37th day, test bleeds were obtained from the mice for determination of the antibody titers. Electrophysiological studies were performed on the 38th and 39th days. Finally, the mice were sacrificed on the 40th day and lymph node cells were obtained for T cell studies.

Electrophysiological Studies To document the electrophysiological evidence of EAMG, amplitudes of serial muscle action potentials were measured by electromyography (EMG) during the repetitive stimulation of the nerve in immunized mice, using the Mystro EMG system (TECA Corporation). A pair of wire electrodes were surgically implanted, encircling the sciatic nerve, two days before EMG. The nerve was stimulated through the implanted electrodes by 3 Hz trains of supramaximal electric current with a duration of 200 microseconds. The corresponding muscle action potentials were recorded with an electrode subcutaneously inserted over the gastrocnemius muscle. A reference electrode was placed at the ankle. Ether inhalation was used during the surgical and recording procedures. The amplitude of the initial evoked potential (P1) was compared to the third, fourth and fifth potentials, and the potential with the maximum amplitude deviation from the PI on either 3 Hz or 5 Hz stimulation was taken as Ps. The change of the amplitude was calculated as follows:

$$\text{Amplitude change } \% = \frac{(Ps - P1)}{P1} \times 100$$

Students' t-test was used to analyze the differences of amplitude changes between the two groups. A typical myasthenic response of a greater than 10% decrement was considered to constitute an electrophysiological evidence of EAMG. The frequency of electrophysiological EAMG was calculated in each group and analyzed by chi-square test.

Radioimmunoassay

One mg of the synthetic peptide was dissolved in 50 μl dimethylformamide and then diluted with PBS to 25 μg/ml. A solution of Torpedo AChR in PBS was prepared to contain 2.5 μg/ml. Aliquots (50 μl/well) of the peptide or AChR solutions were added to a 96-well microtiter plate (Falcon Micro Test III flexible assay plate, Becton Dickinson, Oxcard, Calif.) and the plates were incubated at room temperature overnight. After washing 3 times with PBS, the plates were blocked with 0.25% bovine serum albumin (BSA) in PBS (50 μl/well) at 37° C. for 90 minutes. The plates were washed again 5 times with PBS and to each well was added 50 μl of the serum from AChR-immunized mice, pre-diluted with PBS containing 0.10% BSA, and the plates were covered and allowed to stand at room temperature overnight. After 5 washes with PBS, 50 μl of rabbit IgG antibodies (2.5 μg/ml) against mouse IgG and IgM (Accurate Chemical Scientific Corporation, Westbury, N.Y.) was added to each well and the plates were incubated at 37° C. for 3 hours. The plates were then washed 5 times with PBS and $^{125}$I-labeled protein A (2×10$^5$ cpm in 50 μl of PBS-0.1% BSA) was added to each well. The plates were incubated for 3 hours at room temperature, after which they were washed and the wells were cut out and counted for bound radioactivity. Pre-immune serum samples, obtained from the mice prior to any experimental treatments, were used as controls to correct for non-specific binding.

T Cell Proliferation Assay

Lymph node cells (LNC) were harvested from the AChR-primed mice of each group ten or eleven days after the last AChR immunization. The cells were suspended in RPMI 1640 (Gibco, Grand Island, N.Y.) containing 1% fresh autologous normal mouse serum. The number of viable cells was determined by vital staining with fluorescein diacetage (Rotman and Papermasters, 1966). Viable LNC (5×10$^5$ cells/well) were co-cultured in triplicate in flat bottom microtiter plates with various concentrations of mitogen, antigen or synthetic peptide in a final volume of 200 μl per well. The antigens used were Torpedo AChR peptides (α1–18 and α125–148, in the dose range 10–40 μg/ml), and Torpedo AChR (dose range, 1.5–6.0 μg/ml). Lysozyme and ovalbumin (100 μg/ml) and synthetic nonsense peptide (ESSGTGIESSGTGI, dose range 10–40 μg/ml) were used as negative controls. Concanavalin A (1 μg/ml) and lipopolysaccharide (500 μg/ml) were used as positive controls to monitor the viability of the cells. After incubation for 3 days at 37° C. in a humidified air/$CO_2$ (19:1) atmosphere, the cultures were pulsed (18 hr) with 1 μCi/well [$^3$H]-thymidine (Research Products International, Mount Prospect, Ill,) and then harvested on to glass microfiber filters (Whatman, Clinton, N.J.) for counting of radioactivity by liquid scintillation.

EXAMPLE I

Synthesis of Peptide Conjugates Sequence ID Nos. 1–7

After purification, MPEG and PVA peptide conjugates were homogeneous molecular species and were confirmed to be free of the uncoupled peptide by HPLC on a size exclusion column (see FIG. 3, for an example). Furthermore, sequence analysis showed that the N-terminal was free in the uncoupled peptides and was completely blocked in the peptide conjugates. It should be noted that these peptides contained all possible amino acids. Furthermore, the attachment of MPEG or PVA to the N-terminal did not preclude the formation of intramolecular disulfide bonds in appropriate peptides (peptides 5 and 6 in FIG. 1). It is, therefore, clear that this reaction should be universally applicable to coupling MPEG or PVA to any other synthetic peptide.

The present invention allows the preparation of peptide conjugates to mPEG or PVA by using a coupling reaction which ensured that the mPEG was linked to the peptide via its α-aimino group on the N-terminal amino acid while the peptide is Still attached to resin. This method provided a 1:1, tail-to-head (mPEG or PVA to peptide), monomeric conjugate of high purity. As noted previously, however, chemistries designed to mPEG derivatize the peptides of the invention at the carboxy terminus or at both the amino and carboxy termini are known to those of skill in the art and are expressly included within the scope of the present invention.

All the amino acid side chains within the conjugate, except for the N-terminal, remained unaltered and, because they were not attached to mPEG or PVA groups, they were capable of participating in immune recognition and epitope-specific immunoregulatory mechanisms. In contrast to the methods of the invention, mPEG-protein conjugates have been made by coupling MPEG to the protein, usually via ϵ-amino groups of lysine residues (Wei et al, 1981; Nordvall et al, 1986; Holford-Strevens et al, 1987; Jackson et al, 1987). This results in multiple substitutions on the protein surface and in modification of a number of lysine residues. The product would be expected to contain a mixture of molecular species of derivatives. The use of such compounds as tolerogens would potentially give rise to serious problems in reproducibility and efficacy, particularly in the recognition of individual epitopes by the immune system.

The general approach of epitope directed immunosuppression by well-defined tolerogenic peptide conjugates offers useful refined strategies for modulation of antibody responses to immunopathogenic sites on multi-determinant complex protein antigens. Because it provides a means to suppress the production of antibodies against the pathogenic epitopes, it should be applicable to autoantigens, alloantigens and allergens. mPEG itself does not seem to have any harmful or toxic effects in humans. Allergens conjugated to mPEG have already been safely administered to human subjects suffering from asthma (Mosbech et al, 1990) and honeybee venom allergy (Muller et al, 1987). Thus, the invention methods of MPEG or PVA conjugation to peptides should prove important, if not essential, for the employment of these peptide conjugates in specific tolerance to epitopes of protein antigens.

EXAMPLE II

Specific Peptide Uses

Figure 6:
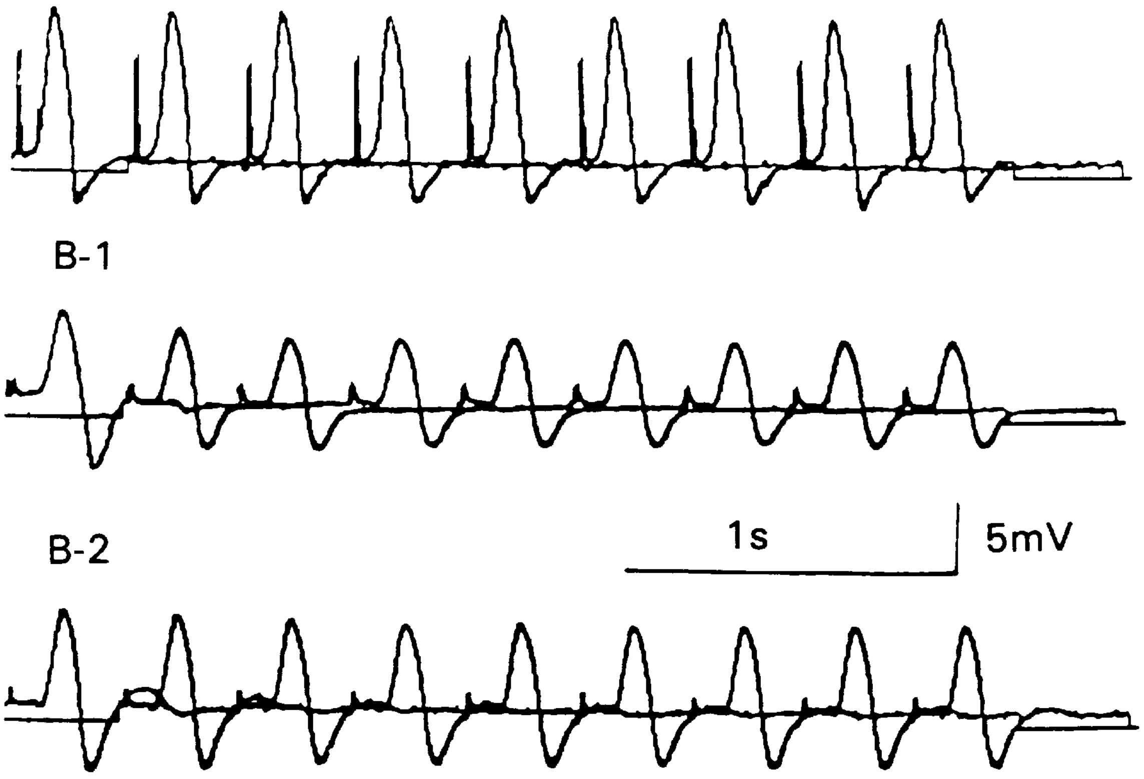
FIG. 6. An example of electrophysiological findings from a normal mouse and an EAMG-positive mouse. (A) EMG response of a normal mouse to a train of 3 Hz repetitive stimulation. (B1) a typical decremental response (−33%) in an EAMG-positive mouse. (B2) the decremental amplitude in B1 was substantially restored towards normal (−13%), 3 minutes after an intraperitoneal injection of 250 μg edrophonium chloride.
Figure 7:
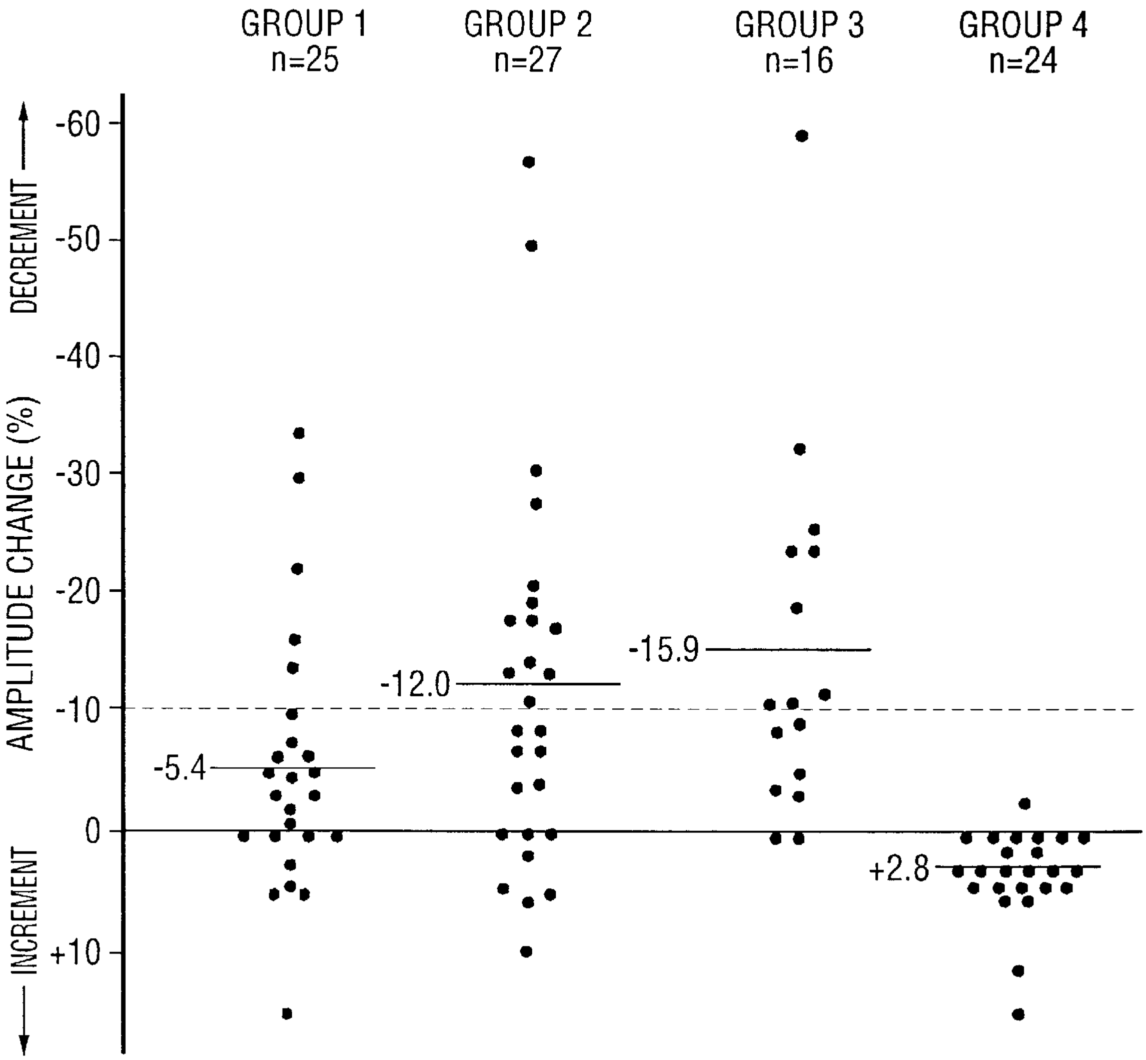
FIG. 7. Effects of prior administration of mPEG-(α125–148) on the development of electrophysiological EAMG after immunization with AChR (see FIG. 4). Note that in Group 1 mice, both the mean amplitude change and the proportion of mice showing greater than 10% decrement were smaller than Groups 2 or 3 ($p<0.05$), but greater than Group 4, mice ($p<0.05$), suggesting that the mPEG-(α125–148) conjugate suppresses development of electrophysiological EAMG but the suppression was incomplete.
Figure 8A:
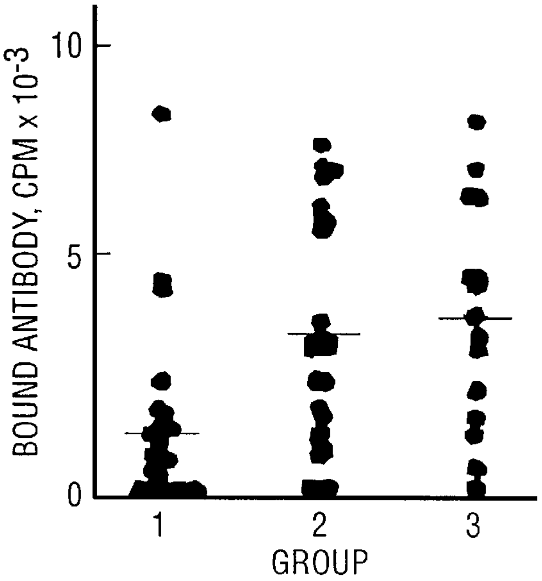
FIG. 8. Effects of pre-administration of mPEG-(α125–148) on the antibody response to immunization with AChR. The anti-AChR antisera from the three groups of mice (Groups 1–3) were studied for antibody binding to: (A) peptide α125–148; (B), whole AChR; (C) peptide α45–60 and (D) peptide α182–198 as described in the text. In A, Group 1 mice showed significant suppression of the antibody population that binds with peptide α125–148 (mean net cpm±standard deviation=1414 ±1801 compared to the mice in Group 2 (3334±2318, $p<0.005$) and Group 3 (3626+2214, $p<0.005$). Antibodies against whole receptor (shown in B; $P>0.5$), peptide α45–60 (shown in C; $P>0.1–0.5$) and peptide α182–198 (shown in D; $P>0.1–0.5$) suffered no significant suppression in Group 1 compared to the control groups.
Figure 8B:
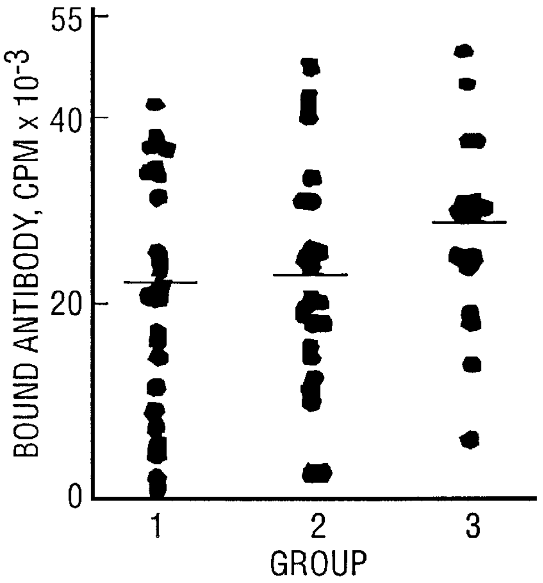
Figure 8C:
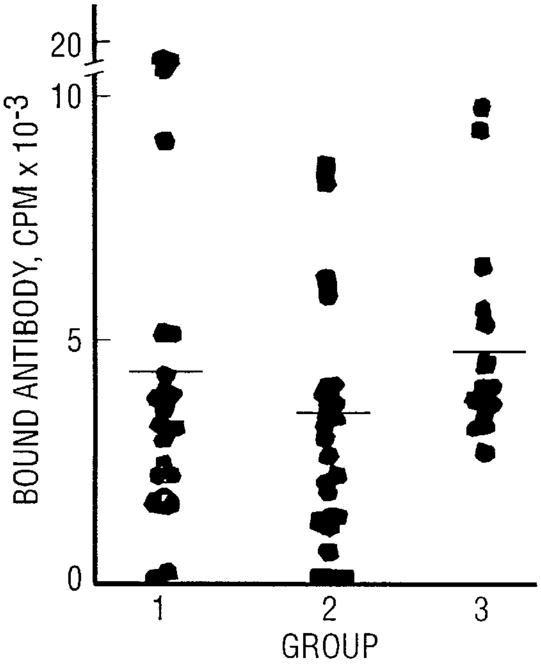
Figure 8D:
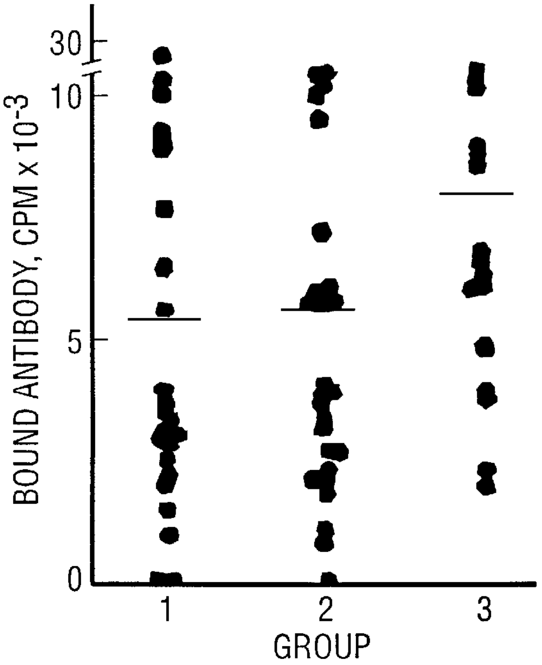

Effect of the mPEG-(α125–148) Conjugate on the Development of Electrophysiological EAMG Although some immunized mice showed muscle weakness, quantitative assessment of muscle weakness was difficult and, therefore, muscle action potentials were measured by EMG. Groups 1, 2 and 3 consisted of 25, 27 and 16 mice, respectively. Additional 24 mice received no intraperitoneal injections or immunizations (Group 4). The typical myasthenic decremental response was reversible upon intraperitoneal injection of 250 μg edrophonium chloride (FIG. 6). The results are summarized in FIG. 7. None of the mice in Group 4 showed a decremental response of the compound action potentials greater than 10%, and their lean amplitude change was +2.8% (i.e. 2.8 increment). Five (20%) of the 25 mice in Group 1 showed a decremental response greater than 10%, while 13 (48%) of the 27 mice of group 2 and 9 (56%) of the 16 mice of Group 3 developed the decremental response. The differences between Group 1 and groups 2 or 3 were statistically significant ($p<0.05$, chi-square test), but were insignificant between Group 2 and Group 3. The mean amplitude change in Group 1 was −5.4% (i.e. a 5.4% decrement), which was significantly smaller than that in Group 2 (−12.0%; $p<0.05$) or Group 3 (−15.9%; $p<0.05$), but greater than in Group 4 (+2.8%; $p<0.05$).

Effects of Pretreatment with mPEG-(α125–148) on the Antibody Response

Figure 9:
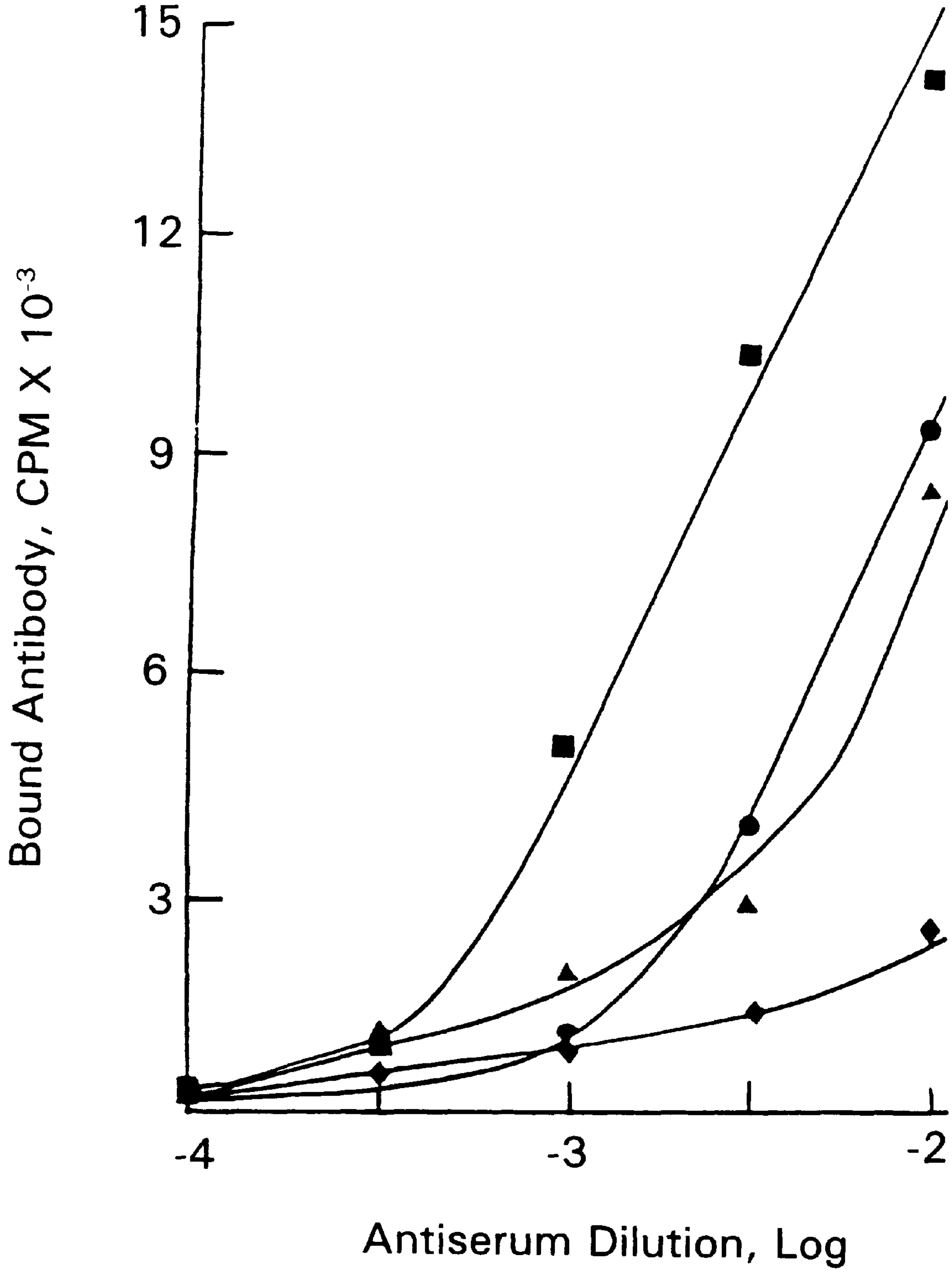
FIG. 9. Binding to peptide α125–148 of anti-AChR antibodies in pooled antisera from each group of mice (see FIG. 6). Antisera were studied at various dilutions as shown. The pooled antisera from Group 1 mice (♦) showed considerably lower antibody binding to the peptide than antibodies from Groups 2 (●), 3 (■), and 5 (▲) (see text).

The results of antibody binding to AChR and to selected regions of the α chain are summarized in FIG. 8. The antibodies bound to peptide α125–148 (FIG. 8A) were significantly decreased in the anti-AChR antisera from the group of mice which received the mPEG-(α125–148) conjugate (Group 1) prior to immunization with Torpedo AChR, whereas mice that had received mPEG-nonsense peptide (Group 2) or free α125–148 (Group 3) prior to AChR immunization exhibited no decrease in the antibodies directed against this region (FIG. 8A). Antibodies bound to whole Torpedo AChR (FIG. 8B), to peptide α45–60 (FIG. 8C) and to peptide α182–198 (FIG. 8D) were not significantly different among the three groups ($p>0.1$). To further confirm the epitope specific suppression of the antibody response, serum samples of the mice within each group were pooled and used in serial dilutions for determining the levels of antibodies against the region α125–148 (FIG. 9). The antiserum mixture from Group 1 [pretreated with mPEG-(α125–148)] had consistently lower amounts of antibody binding as compared to the antiserum mixture from Group 2 (pretreated with mPEG-Nonsense peptide) and group 3 (pretreated with unaltered free α125–148) and an additional group of mice without any treatment prior to the immunizations with AChR (Group 5). The antibody levels in Group 3 were consistently greater than the other two controls. Antibodies against peptide α125–148 were not detectable in Group 4 mice.

Figure 10A:
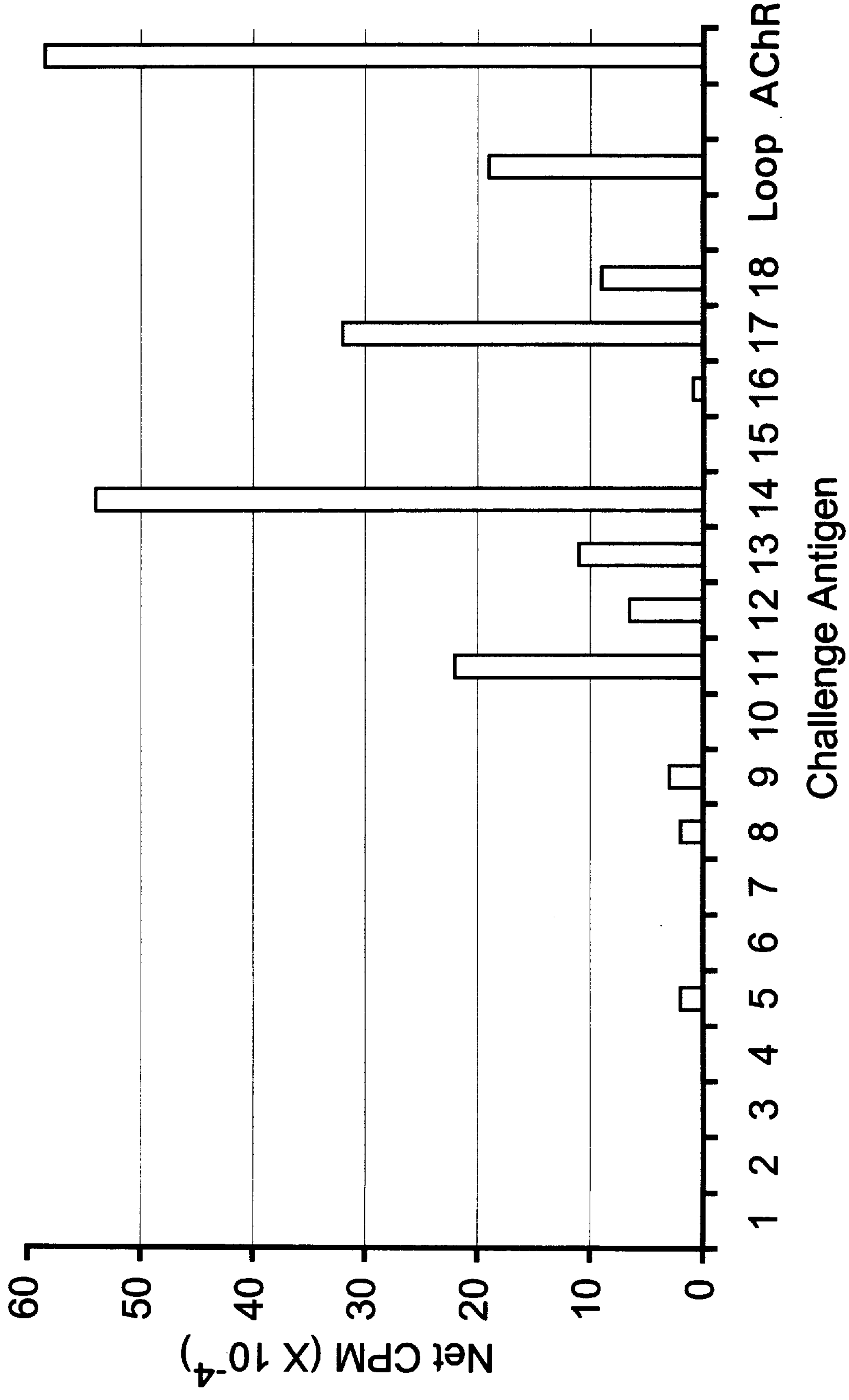
FIG. 10. Effects of pre-administration of mPEG-(α125–148) on the T cell proliferative responses after immunization with AChR. The T-cell recognition profiles of EAMG-negative mice (C57/BL6) from Group 1 and EAMG-positive mice from Group 2 were mapped with uniform sized, overlapping synthetic peptides corresponding to the entire extracellular part of the a chain of Torpedo AChR (Mulac-Jericevic et al., 1987a,b) and with peptide α125–148 (loop) (McCormick and Atassi, 1984). In these assays LNC ($5\times10^5$ cells/well) were challenged in vitro with various doses of peptide (10–40 μg/ml), AChR (1.5–6.0 μg/ml). Nonsense peptide, lysozyme and ovalbumin were used as negative controls and added to the cells in the same dose ranges for peptides and AChR, respectively. Concanavalin A (1 μg/ml) was used as a positive control. The results were done in triplicate and repeated twice. EAMG-positive and EAMG-negative mice were selected on the basis of the EMG test.
Figure 10B:
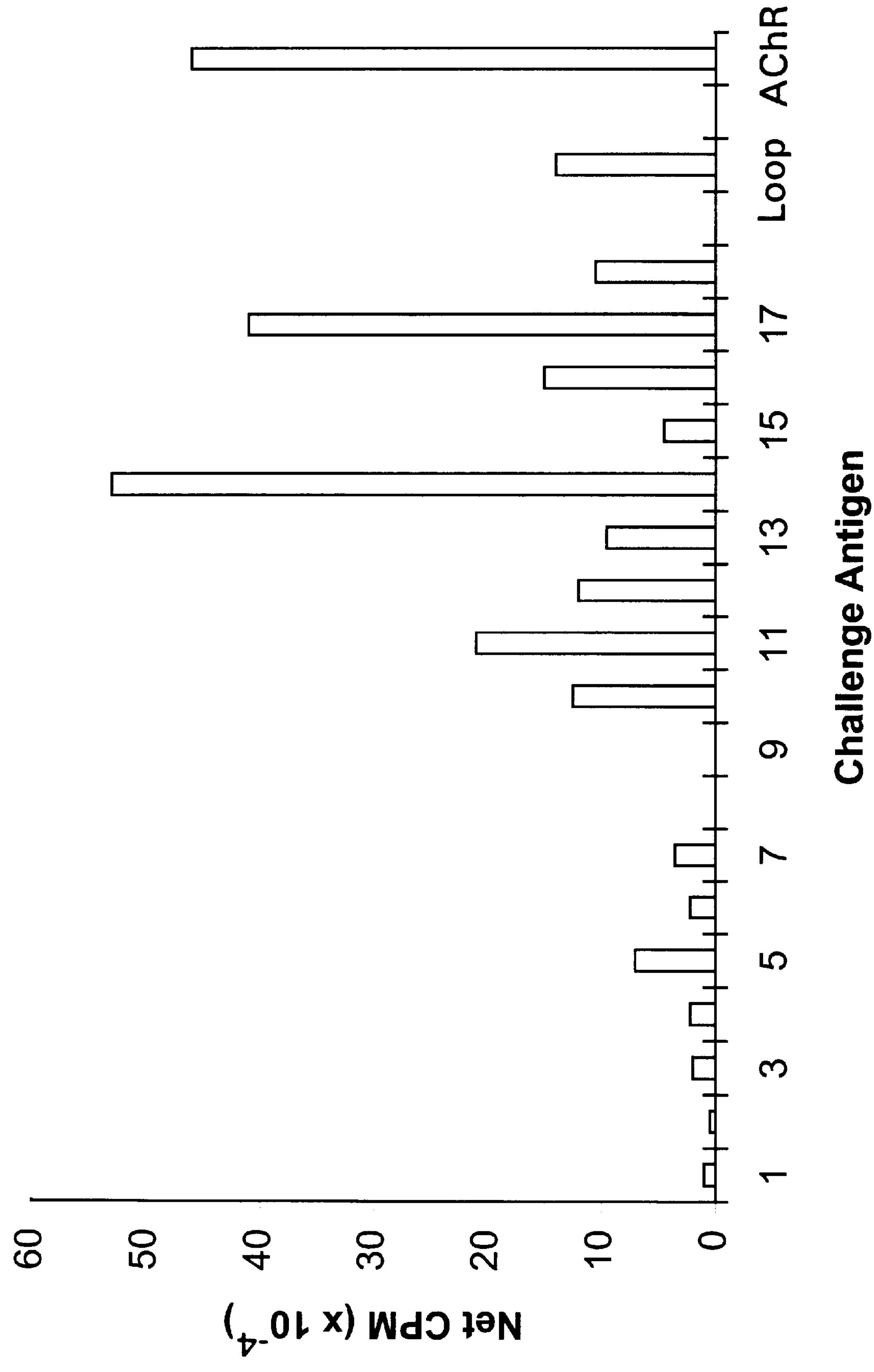

Effect of Pretreatment with mPEG-(α125–148) on the T Cell Proliferative. Response The profiles of T-cell responses in EAMG-positive (pretreated with mPEG-Nonsense peptide) and EAMG-negative mice which had been treated with mPEG(α125148) were mapped with the synthetic overlapping peptides corresponding to the main extracellular domain (residues 1–210) of the a chain of Torpedo AChR. Lymph node cells from each group of mice were pooled separately based on their electrophysiological status for EAMG. The T cell proliferation profiles did not show meaningful differences among the groups regardless of their electrophysiological status (FIG. 10). The peptide recognition profile by AChR-primed T cells obtained here is in agreement with the profile previously reported for this mouse strain (Yokoi et al., 1989; Pachner et al., 1989).

Autoantibody-mediated mechanisms which have been demonstrated at the motor end plates in both EAMG and human myasthenia gravis include 1) pharmacological blockade of the acetylcholine binding site; 2) an increased rate of receptor degradation due to cross-linking of adjacent receptors, 3) an activation of the complement-mediated membrane lysis and 4) an alteration of the ion channel properties of the receptor (Ashizawa and Appel 1985). Previous studies with synthetic α125–148 and with overlapping synthetic peptides which comprised the entire extracellular domain of the a subunit of AChR have illustrated the pharmacological (Lennon et al., 1985) and immunological (Lennon et al., 1985; Mulac-Jericevic et al., 1987) importance of this region. The sequence of the region α125–148 is highly conserved among species. It binds acetylcholine (McCormick and Atassi, 1984) and contains a universal binding region for long and short α-neurotoxins (Mulac-Jericevic and Atassi, 1987b; Ruan et al., 1990, 1991). Because of its direct involvement in the binding of acetylcholine and since the affinity of the antibodies to the receptor is several orders of magnitude higher than that of acetylcholine, the antibodies are capable of effectively blocking the acetylcholine binding site. Thus, the inventors reasoned that suppression of the antibody response to this region might alleviate the pharmacological blockade of the acetylcholine binding site, leading to the suppression of the development of EAMG.

It has been shown (Abuchowski et al., 1977; Lee and Sehon, 1977, 1978a; King et al., 1977, 1979; Davis et al., 1980; Sehon, 1989) that antibody responses to proteins can be modulated by protein-mPEG conjugates. It was not known, however, whether the approach may be used to obtain epitope-specific suppression of antibody responses to a preselected region of a protein. The results disclosed here demonstrate that injections of mice with mPEG-(α125–148) suppressed the development of electrophysiological EAMG induced by subsequent immunizations with whole Torpedo AChR, and this was accompanied by a suppression of autoantibody responses restricted to α125–148. These findings suggest that suppression of the antibody responses against this region rescued acetylcholine-binding sites on AChR from blockade by such antibodies. Other mechanisms may also play a role, however. Antibodies against the a subunit may be twice as likely to cross-link the adjacent receptors as antibodies against the other subunits, since the AChR is a pentamer consisting of two a subunits and one each of the β, γ and δ subunits. Because of this, and the fact that the region α125–148 is a major site of recognition by autoantibodies in EAMG, it is very likely that the population of antibodies directed against this region plays an important role in the development of EAMG through accelerated receptor degradation. Likewise, the decrease in this population of autoantibodies may lead to attenuation of the other pathophysiological mechanisms in EAMG.

The suppression of the electrophysiological EAMG was incomplete. Since the suppression of the antibody responses; to region α125–148 was also incomplete, the remaining antibody activities against this region can partially account for the residual disease activity. Antibodies directed against other epitopes were not suppressed by the mPEG-(α125–148) conjugate and may also produce alterations of the synaptic transmission at the motor end plates through accelerated receptor degradation or by allosteric effects on the acetylcholine binding site and would thus have pathogenic activities.

Pretreatment with the mPEG-(α125–148) conjugate, followed by immunization with whole AChR, caused specific decrease of antibody responses directed against region α125–148, suggesting that the conjugate induces immunosuppression through the regulatory mechanisms involving specific epitope recognition. One of the first steps in immune regulation takes place in the presentation of epitopes to T cells by antigen presenting cells. It has been shown (Holford Strevens et al, 1987), in mice which had developed tolerance to native ovalbumin via intraperitoneal injections of an ovalbumin-mPEG conjugate, that the presentation of mPEG-modified antigen to T helper (Th) cells by peritoneal adherent cells was less efficient than the presentation of native antigen. However, since changes in the T-cell responses to α125–148 or to other AChR α-chain regions were not detected, it is unlikely that the presentation of mPEG-(α125–148) to Th cells is impaired. Another mechanism of tolerogenicity caused by the mPEG-(α125–148) conjugate may involve T suppressor (Ts) cells. A passive transfer of specific Ts cells activated by mPEG-antigen conjugates to syngeneic mice has been shown to cause antigen-specific immunosuppressiorn in the recipient animals, suggesting that induction of antigen-specific Ts cells and release of suppressor lymphokines from these cells may play important roles (Lee et al., 1981; Mokashi et al., 1989; Sehon et al., 1989). Further experiments are needed to elucidate the role, if any, of Ts cells in the immunosuppression caused by the mPEG-peptide conjugate. Immunosuppression of antibody responses mediated by an mPEG-epitope conjugate may also operate at the level of T-B cell collaboration due to impairment of direct contact of the epitope-specific B cells with the conjugate resulting in central tolerance (Sehon and Lang, 1986). Differences might be expected, however, between the presentation and recognition of mPEG-protein conjugates and mPEG-peptide conjugates because of profound differences in their architecture.

In conclusion, these data suggest that mPEG-modified peptides corresponding to pathogenic autodeterminants of AChR may promise an effective immunospecific treatment for myasthenia gravis in the future. Furthermore, the general approach of epitope directed immunosuppression by well-defined tolerogenic mPEG-peptide conjugates offers useful refined strategies for modulation of antibody responses to immunopathogenic sites on multideterminant complex protein antigens. Because it provides a means to suppress the production of antibodies against the pathogenic epitopes, its application should not be restricted to autoantigens or alloantigens but should also be applicable to allergens. mPEG itself does not seem to have any harmful or toxic effects in humans.

EXAMPLE III

Clinical Applications of Epitope-Specific Suppression of Antibody Responses in Immune Diseases

Methods of Treatment

Allergens conjugated to mPEG have already been safely administered to human subjects suffering from asthma (Mosbech et al., 1990) and honeybee venom allergy (Muller et al., 1987) with therapeutic effects [these references as they pertain to methods, of treatment of patients with undesirable immune responses, are specifically incorporated by reference herein]. Sehon (1988) has suggested new clinical applications of mPEG conjugates to arrest the progress of HIV infection to full blown acquired immunodeficiency syndrome (AIDS) in asymptomatic HIV-seropositive individuals. As opposed to the treatment protocols suggested in these prior art approaches which were limited by the masking of the epitopes by the tolerogenic polymer, the present invention exposes the epitope without masking or altering the conformation of a whole native polypeptide antigen (Sehon 1988).

A method of treatment for an immune disease such as myasthenia gravis, thus, is likely to follow closely these previous drug treatment protocols which used whole antigen. These approaches would be followed except that one would take advantage of the substantial improvement of there being no requirement to take into consideration the masking of the epitopes on the surface of the derivatized whole antigen. Thus, as in Sehon (1988) it was anticipated that the antigen binding capacity of antibodies directed against the allergen would be markedly reduced if not totally impaired as a result of conjugation of the allergen with mPEG. For that reason, in previous studies it was necessary to ensure the efficacy of the antibodies directed to the allergen by including a two-phase approach. In the first stage (immunosuppressive), a series of injections of tolerogenic mPEG conjugates of the antigen would be made for the induction of the immunosuppression as to the various epitopes represented on the whole antigen. In the second (effector) stage, a series of non-conjugated antigens would be injected, either with or without intermittent injections of the tolerogenic derivatives.

In the present invention, since there is no masking of the epitope by the tolerogenic polymer, there is no need to follow the injection of mPeg conjugated peptide epitopes with non-conjugated peptides. This represents a substantial improvement over the prior art approaches. These reagents will then be prepared into a vaccine.

Vaccine Preparation and Use

Immunogenic compositions, believed to be suitable for use as an anti-immune vaccine, may be most readily prepared directly from peptides or peptide analogs of epitopes synthetically prepared and purified in a manner disclosed herein. Preferably the purified material is also extensively dialyzed to remove undesired small molecular weight molecules and/or lyophilization of the thus purified material for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations or aerosols. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The active ingredient will commonly be used as 0.05 to 0.1 percent solution in phosphate buffered saline, admixture with synthetic polymers of sugars (Carbopol) used as 0.25 percent solution, aggregation of the protein in the vaccine by that treatment with temperatures ranging between 70° to 101° C. for 30 second to 2 minute periods respectively. Aggregation may be accomplished by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

EXAMPLE IV

Method for Screening Potential Reagents for Efficacy in Treatment of Immune Diseases

Immunoassays

It is proposed that the antigenic peptides or analogs of the same peptides of the invention will find utility as immunogens in connection with vaccine development, or as antigens in immunoassays for the detection of anti-peptide antigen-reactive antibodies. Turning first to immunoassays, in their most simple and direct sense, preferred immunoassays of the invention include the various types of enzyme linked immunosorbent assays (ELISAs) known to the art. However, it will be readily appreciated that utility is not limited to such assays, and useful embodiments include RIAs and other non-enzyme linked antibody binding assays or procedures.

In the preferred ELISA assay, peptides incorporating the native antigen sequences (epitopes) are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA) or casein onto the well that is known to be antigenically neutral with regard to the test antisera. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a second antibody having specificity for the first. Of course, in that the test sample will typically be of human origin, the second antibody will preferably be an antibody having specificity in general for human Ig. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azido-di-(3-ethylbenzthiazoline-6-sulfonic acid [ABTS] and $H_2O_2$, in the case of peroxidase as the enzyme label. Quantification is then achieved by measuring the degree of color generation, e.g., using a visible spectra spectrophotometer. It will, of course, be known to those skilled in the art that the chromatogenic protocol outlined above may be substituted by a radiological procedure such as the use of radioactive isotopes of iodine.

Screening Assays

An important aspect of the invention is the use of methods of the invention in screening assays for the identification of substances which may immunosuppress or otherwise modify or alter the undesirable immune response. The use of synthetically produced peptides (epitopes) is of particular benefit because the naturally occurring antigen may only be present in only small quantities and may difficult to purify from other immunogenic substances. Moreover, this allows one a ready source of a wide range of potential epitopes representing various regions on the surface of a polypeptide antigen.

The invention also provides access to human epitopes which may be difficult to produce otherwise if one is limited to collection of the native antigen from human tissues. Even so, by use of the human-derived epitopes in animal models, the sensitivity to various candidate substances can be first screened prior to human trials. The importance of this is quite significant in that it indicates that where one seeks to identify a compound, e.g., that may function to immunosuppress the disease in man, that one should employ human version of a particular epitope of a particular antigen for the screening assay.

The screening assays of the invention, in preferred embodiments, conveniently employ the animal model most directly mimicking the disease in humans. The battery of tests shown in Example II above for the disease model for myasthenia gravis are illustrative of the types of tests that can be used, e.g., electophysiological studies, radioimmunoassays, T-cell proliferations assays, etc.

In that most such screening assays in accordance with the invention will be designed to identify agents useful in inhibiting the undesirable immune response, preferred assays will typically employ the native antigen from which the peptides are derived in some aspect. Thus, it is preferred that a source of the native antigen be available.

There are believed to be a wide variety of embodiments which can be employed to determine the effect of a candidate substance such as a tolerogenic epitope-specific peptide on the immune disease of the invention, and the invention is not intended to be limited to any one such method. However, it will generally be desirable to employ a system wherein one can measure the ability of the candidate substance to immunosuppress the disease symptoms in the model.

One method employed by the inventors uses a mouse model for the screening of candidate epitopes capable of suppressing the experimental disease symptoms in mice. Similar studies have been accomplished using rat models of human allergy responses to Ra3. As mentioned previously, Grave's disease has well-known animal analogs.

In preferred assays, the admixture containing the tolerogenic peptide is injected at various intervals into a test subject and allowed to immunosuppress for a selected amount of time, and the resultant animals are tested for reduction of symptoms of the particular immune disease. Then, one simply measures the amount of each reduction in symptoms of the disease, e.g., versus a control to which no candidate substance has been injected. This measurement can be made at various time points where dosage rate data is desired. From this, one may determine the ability of the candidate substance to alter or modify the immune response of the disease.

REFERENCES CITED

The following references to the extent that they provide procedural details supplementary to those set forth herein, are specifically incorporated herein by reference.

Abuchowski, A., van Es., T., Palczuk, N. C. and Davis, F. F. (1977) *J. Biol. Chem.* 252, 3578.

Anzinger and Mutter, *Polymer Bulletin* 6:595 (1982)

Ashizawa, T. and Appel, S. H. (1985) *Springer Sem Immunopathol.* 8, 177–196.

Atassi, H. and Atassi, M. Z. *FEBS Lett.* 188:96 (1985).

Atassi, H. and Atassi, M. Z. *Europ. J. Immunol.* 16:229 (1986).

Atassi, M. Z. and Saplin, B. J. (1968) *Biochemistry* 7, 688–698.

Atassi, M. Z., Manshouri, T. and Sakata, S. (1991) *Proc. Natl. Acad. Sci.* USA 88, 3613.

Atassi, M. Z., Manshouri, T. (1992) *J. Prot. Chem.*, in press.

Atassi, M. Z., Ruan, J. H., Jinnai, K., Oshima, M. and Ashizawa, T., *Proc. Ntl. Acad. Sci. USA* (1992), submitted Becker and Bayer, *J. Am. Chem. Soc.* 101:239 (1979)

Davis, F. F., Abuchowski, A., van Es, T., Palczuk, N. C., Savoca, K., Chen, R. H -L and Pyatuk, P., In "*Biochemical Polymers: Polymeric Materials and Pharmaceuticals for*

*Biomedical Use*" (E. P. Goldberg and A, Nakajima, Eds.), pp. 441–452. Academic Press, New York, 1980.

Froehner, S. C. and Rafto, M. Z. (1979) *Biochemistry* 18, 301–307.

Holford-Strevens, V., Jackson, C. -J. C., Charlton, J., Akiyama, K. A., Lang, G. M., Carter, B. G. and Sehon, A. H. (1987) Cellular Immunology 104, 245–254.

Jackson, C. -J. C., Charlton, J. L., Kuzminski, K., Lang, G. M. and Sehon, A. H. (1987) *Analytical Biochemistry* 165, 114–127.

Kaiser, E., Colescott, R. L., Bassinger, C. D. and Look, D. T. (1970) *Anal. Biochem.* 34, 595–598.

King, T. P., Kochoumian, L. and Lichtenstein, L. M. (1977) *Arch. Biochem. Biophys.* 178, 442.

King, T. P., Kochoumian, L. and Chiroazzi, N. (1979) *J. Exp. Med.* 149, 424.

Kita, et al., *Drug Design Delivery* 6:157 (1990)

Kurisaki, et al. *Europ. J. Immunol.* 16:236 (1986).

Kyte and Doolittle, *J. Molec. Biol.* 157:105 (1982).

Laemmli, U. (1970) *Nature* (London) 266, 680–685.

Lee, W. Y. and Sehon, A. H. (1977) *Nature* (London) 267, 618.

Lee, W. Y. and Sehon, A. H. (1978a) *Arch. Allergy Appl. Immunol.* 56, 159.

Lee, W. Y. and Sehon, A. H. (1978b) *Arch. Allergy Appl. Immunol.* 56, 193.

Lee, W. Y., Sehon, A. H. and Akerblom, E. (1981) *Int. Arch. Allergy Appl. Immunol.* 64, 100.

McCormick, D. J. and Atassi, M. Z. (1984) *Biochem. J.* 224, 9950–10000.

Mokashi, S., Holford-Strevens, V., Sterrantino, G. and Jackson, C. J. (1989) *Immunol. Lett.* 23, 95–102.

Mosbech, H., Dirksen, A., Dreborg, S., Frlund, L., Heinig, J. H. Svendsen, U. G., Sborg, M., Taudorf, E. and Weeke, B. (1990) *Allergy* 45, 142–150.

Mulac-Jericevic, B. and Atassi, M. Z. (1987) *J. Prot. Chem.* 6, 365–373.

Mulac-Jericevic, B. and Atassi, M. Z. (1987a) *Biochem. J.* 248, 847–852.

Mulac-Jericevic, B. and Atassi, M. Z. (1987b) *J. Prot. Chem.* 6, 365–373.

Mulac-Jericevie, B., Kurisaki, J. and Attasi, M. Z. (1987) *Proc. Natl. Acad. Sci. USA* 84, 3633–3637.

Muller, U., Rabson, A. R., Bischof, M., Lomnitzer, R., Dreborg, S. and Lanner, A. (1987) *J. Allergy Clin. Immunol.* 80, 252–261.

Nishimura, et al., *Life Sciences* 33:1467 (1983).

Noda, M., Takahashi, H., Tanabe, T., Toyosato, M., Furutani, Y., Hirose, T., Asai, M., Inayama, S., Miyata, T. and Numa, S. (1982) *Nature* (London) 299, 793–797.

Nordvall, S. L., Uhlin, T., Ohman, S., Bjorkander, J., Malling, H -J., Week, B., Dreborg, S., Lanner, A. and Einarsson, R. (1986) *Allergy* 41, 89–94.

Pachner, A. P., Kantor, F. S., Mulac-Jericevic, B. and Atassi, M. Z. (1989) *Immunology Letters* 20, 199–204.

Ruan, K. -H., Spurlino, J., Quiocho, F. A. and Atassi, M. Z. (1990) *Proc. Natl. Acad. Sci. USA* 87, 6156–6160.

Ruan, K. -H., Stiles, B. G. and Atassi, M. Z. (1991) *Biochem. J.* 274 849–854.

Sakakibara, S., Shimonishi, Y., Kishida, T., Okada, M. and Sugihara, H. (1967) *Bull. Chem. Soc. Japan* 40, 2164.

Sartore, et al., *Appl. Biochem. Biotechnol.* 27:55 (1991).

Sehon, A. H. (1989) *Adv. Exp. Med. Biol.* 251, 341–351.

Sehon, A. H. and Lang, G. M., *In Mediators of Immune Regulation and Immunotherapy* (S. K. Singhal and T. L. Delovitch, Eds.) pp. 190–203, Elsevier, New York, 1986.

Sehon, In *Immunobiology of Proteins and Peptides V-Vaccines: Mechanisms, Design, and Applications*, ed. M. Z. Atassi, pp. 341, Plenum Press, New York (1988).

Ueyama, et al., *Polymer J.* 17:721 (1985).

Wei, S. I., Wei, C. W., Lee, W. Y., Filion, L. G., Sehon, A. H. and Akerblom, E. (1981) *Int. Arch. Allergy Appl. Immunol.* 64, 84–99.

Yokoi, T., Mulac-Jericevic, B., Kurisaki, J. T. and Atassi, M. Z. (1987) *Europ. J. Immunol.* 17, 1697–1702.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, it will be understood that one way synthesize the peptides of the invention or one may obtain peptide fragments which are either wholly or partially a fragment of a native antigen or a recombinant derivative of such. Additionally, while the amino acid sequence selected for a given peptide will typically occur as such in the native antigen, it will be understood that one may choose to substitute similar hydropathic amino acids and that the peptide may contain non-linear portions (i.e., such a peptide may represent a discontinuous epitope) of a given antigen, alloantigen or allergen. Similarly, one may wish to add amino acid residues to either one or both termini of the epitope proper which amino acid residues are not relevant to the specificity of the epitope but otherwise facilitate its use or ease of purification, for instance. It is also understood that the tolerogenic polymer molecule may be coupled either to the N-terminal α-$NH_2$ group or to the C-terminal carboxyl group or, in certain cases, to both termini. All such modifications are intended to be included within the scope of the appended claims.

```
SEQUENCE LISTING

(1) GENERAL INFORMATION:

   (iii) NUMBER OF SEQUENCES: 7

(2) INFORMATION FOR SEQ ID NO:1:

     (i) SEQUENCE CHARACTERISTICS:
          (A) LENGTH: 15 amino acids
          (B) TYPE: amino acid
          (D) TOPOLOGY: linear
```

-continued (ii) MOLECULE TYPE: peptide (xi) SEQUENCE DESCRIPTION: SEQ ID NO:1:

Gly Lys Val Tyr Leu Val Gly Gly Pro Glu Leu Gly Gly Trp Lys
1 5 10 15

(2) INFORMATION FOR SEQ ID NO:2:

(i) SEQUENCE CHARACTERISTICS:
(A) LENGTH: 15 amino acids
(B) TYPE: amino acid
(D) TOPOLOGY: linear (ii) MOLECULE TYPE: peptide (xi) SEQUENCE DESCRIPTION: SEQ ID NO:2:

Glu Val Trp Arg Glu Glu Ala Trp His Ala Cys Asp Ile Lys Asp
1 5 10 15

(2) INFORMATION FOR SEQ ID NO:3:

(i) SEQUENCE CHARACTERISTICS:
(A) LENGTH: 15 amino acids
(B) TYPE: amino acid
(D) TOPOLOGY: linear (ii) MOLECULE TYPE: peptide (xi) SEQUENCE DESCRIPTION: SEQ ID NO:3:

Pro Gly Gly Pro Asp Arg Phe Thr Leu Leu Thr Pro Gly Ser His
1 5 10 15

(2) INFORMATION FOR SEQ ID NO:4:

(i) SEQUENCE CHARACTERISTICS:
(A) LENGTH: 15 amino acids
(B) TYPE: amino acid
(D) TOPOLOGY: linear (ii) MOLECULE TYPE: peptide (xi) SEQUENCE DESCRIPTION: SEQ ID NO:4:

Thr Pro Gly Ser His Phe Ile Cys Thr Lys Asp Gln Lys Phe Val
1 5 10 15

(2) INFORMATION FOR SEQ ID NO:5:

(i) SEQUENCE CHARACTERISTICS:
(A) LENGTH: 24 amino acids
(B) TYPE: amino acid
(D) TOPOLOGY: circular (ii) MOLECULE TYPE: peptide (ix) FEATURE:
(A) NAME/KEY: Disulfide-bond
(B) LOCATION: 4..18
(D) OTHER INFORMATION: /note= "internal disulfide linkages creating peptide loop"

(xi) SEQUENCE DESCRIPTION: SEQ ID NO:5:

Lys Ser Tyr Cys Glu Ile Ile Val Thr His Phe Pro Phe Asp Gln Gln
1 5 10 15

Asn Cys Thr Met Lys Leu Gly Ile
20

(2) INFORMATION FOR SEQ ID NO:6:

-continued

```
     (i) SEQUENCE CHARACTERISTICS:
          (A) LENGTH: 15 amino acids
          (B) TYPE: amino acid
          (D) TOPOLOGY: circular

    (ii) MOLECULE TYPE: peptide

    (ix) FEATURE:
          (A) NAME/KEY: Disulfide-bond
          (B) LOCATION: 4..15
          (D) OTHER INFORMATION: /note= "internal disulfide linkages
               creating peptide loop"

    (xi) SEQUENCE DESCRIPTION: SEQ ID NO:6:

Lys Ser Pro Cys Ala Tyr Lys Glu Pro Glu Thr Thr Val Ala Cys
1               5                   10                  15


(2) INFORMATION FOR SEQ ID NO:7:

     (i) SEQUENCE CHARACTERISTICS:
          (A) LENGTH: 24 amino acids
          (B) TYPE: amino acid
          (D) TOPOLOGY: circular

    (ii) MOLECULE TYPE: peptide

    (ix) FEATURE:
          (A) NAME/KEY: Disulfide-bond
          (B) LOCATION: 4..18
          (D) OTHER INFORMATION: /note= "internal disulfide linkages
               creating peptide loop"

    (xi) SEQUENCE DESCRIPTION: SEQ ID NO:7:

Lys Ser Tyr Cys Glu Ile Ile Val Thr His Phe Pro Phe Asp Gln Gln
1               5                   10                  15

Asn Cys Thr Met Lys Leu Gly Ile
            20
```

COMPLIANCE WITH 37 C.F.R. § 1.821(f)

The content of the paper and computer readable copies containing the Sequence Listings are the same.

What is claimed is:

1. A method of producing a peptide reagent useful in the treatment of myasthenia gravis, wherein said peptide reagent is a tolerogenic polymer-linked peptide the peptide of which is known to or suspected of inducing an immune response responsible for symptoms of myasthenia gravis, the method comprising:

conjugating a resin-linked peptide with a tolerogenic polymer having a single reactive end group available for said conjugation, the peptide of said resin-linked peptide having side chain-protected amino acids, and being covalently linked to said resin via a first terminal amino acid of said peptide, and having a second terminal amino acid opposite said first terminal amino acid which is available for said conjugation with said tolerogenic polymer;

deprotecting said side chain-protected amino acids and cleaving said peptide from said resin to provide a single molecular species of peptide-tolerogenic polymer conjugate;

recovering said peptide-tolerogenic polymer conjugate; and, purifying said peptide-tolerogenic polymer conjugate to provide said peptide reagent.

2. The method of claim 1 wherein said step of conjugating a resin-linked peptide with a tolerogenic polymer is modified by substituting the following step:

conjugating a resin-linked peptide with a tolerogenic polymer having a single reactive end group available for said conjugation, the peptide of said resin-linked peptide being covalently linked to said resin via the carboxyl terminus of said peptide, having side chain-protected amino acids, and having an amino terminus available for said conjugation with said tolerogenic polymer.

3. The method of claim 1 wherein said step of conjugating a resin-linked peptide with a tolerogenic polymer is modified by substituting the following step:

conjugating a resin-linked peptide with a tolerogenic polymer having a single reactive end group available for said conjugation, the peptide of said resin-linked peptide having side chain-protected amino acids, being covalently linked to said resin via a first terminal amino acid of said peptide, and having an $\alpha$-$NH_2$ group opposite said first terminal amino acid which is available for said conjugation with said tolerogenic polymer.

4. The method of claim 1 wherein said conjugating a resin-linked peptide with a tolerogenic polymer having a single reactive end group available for said conjugation, is modified by substituting the following step:

conjugating a resin-linked peptide with a tolerogenic polymer having a single reactive end group available for said conjugation, the peptide of said resin-linked peptide having side chain-protected amino acids, and being covalently linked to said resin via the carboxyl group of a first terminal amino acid of said peptide, and having a second terminal amino acid opposite said first terminal amino acid of peptide available for said conjugation with said tolerogenic polymer, and having the amino acid sequence of SEQ ID NO. 5.

5. The method of claim 1 further comprising prior to said conjugating step:

synthesizing said peptide by covalently linking the carboxy-terminal amino acid of a side-chain protected amino acid to said resin and sequentially adding side chain-protected amino acids to create said resin-linked peptide.

6. The method of claim 1 wherein said conjugating a resin-linked peptide step is modified by substituting the following step:

conjugating a resin-linked peptide with a tolerogenic polymer having a single reactive end group available for said conjugation, the peptide of said resin-linked peptide being covalently linked to said resin via the carboxyl group of a first terminal amino acid of said peptide, having side chain-protected amino acids, and having a second terminal amino acid opposite said first terminal amino acid of said peptide which is available for said conjugation with said tolerogenic -polymer, and being a single predetermined epitope that corresponds to a linear sequence of amino acids found in a native polypeptide.

7. The method of claim 1 wherein said step of conjugating a resin-linked peptide is modified by substituting the following step:

conjugating a resin-linked peptide with a tolerogenic polymer having a single reactive end group available for said conjugation, the peptide of said resin-linked peptide being covalently linked to said resin via the carboxyl group of a first terminal amino acid of said peptide, having side chain-protected amino acids, and having a second terminal amino acid opposite said first terminal amino acid of said peptide available for said conjugation with said polymer, and being a single predetermined native polypeptide subunit of an acetylcholine receptor.

8. The method of claim 1 wherein said step of conjugating a resin-linked peptide is modified by substituting the following step:

conjugating a resin-linked peptide with a tolerogenic polymer having a single reactive end group available for said conjugation, the peptide of said resin-linked peptide being covalently linked to said resin via the carboxyl group of a first terminal amino acid of said peptide, having side chain-protected amino acids, and having a second terminal amino acid opposing said first terminal amino acid of peptide available for said conjugation with said polymer, and being a single predetermined epitope known to or suspected of causing an immune response which is the principal causative agent of symptoms of myasthenia gravis.

9. The method of claim 1 wherein said conjugating a resin-linked peptide is modified by substituting the following step:

conjugating a resin-linked peptide with a tolerogenic polymer selected from the group consisting of monomethoxypolyethylene glycol, other polyethylene glycol derivatives which are only capable of joining end-to-tail with said peptide, polyvinyl alcohol, and polyvinyl alcohol derivatives, the peptide of said resin-linked peptide being covalently linked to said resin via the carboxyl group of a first terminal amino acid of said peptide, having side chain-protected amino acids, and having an $\alpha$-$NH_2$ group opposite said first terminal amino acid of said peptide available for said conjugation with said tolerogenic polymer, and being a single predetermined epitope which is known to or suspected of inducing an immune response responsible for symptoms of myasthenia gravis.

10. A reagent produced by the method of any of claims 1–3 and 5–9.

11. The method of claim 1 further comprising repeating said conjugating, deprotecting, cleaving and recovering steps whereby the same peptide-polymer conjugate is produced, which conjugate is structurally characterized as a single peptide molecule joined end-to-tail with a single molecule of polymer.

12. A method of producing a reagent useful in the treatment of myasthenia gravis wherein said reagent includes a peptide corresponding to a single predetermined epitope which is known to or suspected of inducing a myasthenia gravis autoimmune response, the method comprising:

synthesizing a resin-linked peptide wherein the peptide of said resin-linked peptide is Sequence ID No. 5 with side chain-protected amino acids, and is covalently linked via a carboxy-terminal amino acid of said peptide to said resin;

derivatizing an N-terminal amino acid of said resin-linked peptide with an end terminus of monomethoxypolyethylene glycol (mPEG);

deprotecting the side chain-protected amino acids comprising the peptide;

cleaving the peptide from the resin to provide a peptide-mPEG conjugate in the form of a single molecular species;

recovering the peptide-mPEG conjugate; and, purifying the peptide-mPEG conjugate.

13. A peptide reagent produced by the method of claim 12.

14. The method of claim 12 wherein said derivatizing includes derivatizing an N-terminal amino acid of said peptide with an end terminus of polyvinyl alcohol (PVA) or another tolerogenic polymer capable of only joining end-to-tail with said peptide.

15. A method of producing a peptide reagent useful in the treatment of myasthenia gravis, wherein said peptide reagent is a tolerogenic polymer-linked peptide the peptide of which is an epitope known to or suspected of inducing an immune response responsible for symptom of myasthenia gravis, the method comprising:

conjugating said peptide at its carboxyl or amino terminus to an end terminus of a single immunologically inert polymer molecule, whereby an end-to-end peptide-polymer conjugate is produced which is capable of epitope specific suppression of antibody response to said peptide; and recovering the peptide-polymer conjugate.

16. The method of claim 15 wherein said conjugating comprises attaching said peptide to said polymer by a terminal $\alpha$-$NH_2$ group on said peptide.

17. The method of claim 15 wherein said conjugating comprises:

conjugating the peptide of SEQ ID NO 5 at its carboxyl or amino terminus to an end terminus of a single immunologically inert polymer molecule, whereby an end-to-end peptide-polymer conjugate is produced which is capable of epitope specific suppression of antibody response to said peptide.

18. A peptide-polymer conjugate comprising a single peptide molecule chosen from the group consisting of SEQ ID NOs 1–7 and a single tolerogenic polymer molecule, said peptide being covalently linked by its α-$NH_2$ or —COOH terminus to an end terminus of said polymer molecule, said polymer being chosen from the group consisting of monomethoxypolyethylene glycol (mPEG), polyvinyl alcohol (PVA) and derivatives thereof.

19. A method of producing a tolerogenic peptide-polymer conjugate wherein the peptide of said peptide-polymer conjugate is a single predetermined epitope which is known to or suspected of inducing an immune response, the method comprising:

conjugating a resin-linked peptide with a tolerogenic polymer having a single reactive end group available for said conjugation, the peptide of said resin-linked peptide being covalently linked to said resin via a first terminal amino acid of said peptide, having side chain-protected amino acids, and having a second terminal amino acid opposite said first terminal amino acid available for conjugation with said polymer;

deprotecting the side chain-protected amino acids comprising the peptide;

cleaving the peptide from the resin to provide a single molecular species of peptide-polymer conjugate;

recovering the peptide-polymer conjugate; and purifying the peptide-polymer conjugate.

20. The method of claim 19 wherein said conjugating a resin-linked peptide is modified by substituting the following step:

conjugating a resin-linked peptide with a tolerogenic polymer having a single reactive end group available for said conjugation, the peptide of said resin-linked peptide being covalently linked to said resin via a first terminal amino acid of said peptide, having side chain-protected amino acids, and having a second terminal amino acid opposite said first terminal amino acid of said peptide available for said conjugation with said polymer.

21. The method of claim 19 wherein said conjugating comprises conjugating a resin-linked peptide with a tolerogenic polymer having a single reactive end group available for said conjugation, said polymer chosen from the group consisting of monomethoxypolyethylene glycol, other polyethylene derivatives which are only capable of joining end-to-tail with said peptide, polyvinyl alcohol, and polyvinyl alcohol derivatives, the peptide of said resin-linked peptide being covalently linked to said resin via a first terminal amino acid of said peptide, having side chain-protected amino acids, and having a second terminal amino acid opposite said first terminal amino acid of said peptide available for said conjugation with said polymer.

* * * * *